United States Patent
Kaneko et al.

(10) Patent No.: US 6,410,777 B1
(45) Date of Patent: Jun. 25, 2002

(54) SALICYLIC ACID ESTER DERIVATIVE AND ITS PRODUCTION

(75) Inventors: Hiroaki Kaneko; Wataru Funakoshi; Katsushi Sasaki, all of Yamaguchi (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/402,359

(22) PCT Filed: Apr. 3, 1998

(86) PCT No.: PCT/JP98/01564

§ 371 (c)(1),
(2), (4) Date: Oct. 4, 1999

(87) PCT Pub. No.: WO98/45246

PCT Pub. Date: Oct. 15, 1998

(30) Foreign Application Priority Data

| Apr. 4, 1997 | (JP) | 9-086525 |
| May 7, 1997 | (JP) | 9-116777 |
| May 8, 1997 | (JP) | 9-118080 |
| Feb. 18, 1998 | (JP) | 10-035967 |

(51) Int. Cl.$^7$ .......................... C07C 69/88; C07C 69/96
(52) U.S. Cl. ........................................ 560/68; 558/274
(58) Field of Search ............................. 560/68; 558/274

(56) References Cited

U.S. PATENT DOCUMENTS

| 3,644,480 A | 2/1972 | Kablaoui |
| 3,790,671 A | 2/1974 | Simm |
| 5,696,222 A | 12/1997 | Kaneko et al. |

FOREIGN PATENT DOCUMENTS

| EP | 0 124 905 A1 | 11/1984 |
| EP | 764673 | 3/1997 |
| FR | 1 163 808 | 10/1958 |
| GB | 1358272 | 7/1974 |
| GB | 1388857 | 3/1975 |
| JP | 48-96531 | 12/1973 |
| JP | 52111540 | 9/1977 |
| JP | 06157739 | 6/1994 |
| JP | 95039483 | 5/1995 |
| JP | 10036497 | 2/1998 |

OTHER PUBLICATIONS

Derwent Publication; XP 002157562; Mar. 28, 1995 (JP 7–82592).

Derwent Publication; XP 002157563; Jul. 31, 1991 (JP 3–176425).

Lee et al; "Synthesis of Lipophilic Crown Ethers with Pendant Carboxylic Acid Groups"; XP002157556 (1986); Chemical Abstracts XP002157556.

Guzek et al; "Transdermal Drug Transport and Metabolism. I. Comparison of In Vitro and In Vivo results"; Chemical Abstracts XP002157557 (1989).

Lokhande et al; "Novel Method in Synthesis of 3–phenyl–4–styryl—and 3–phenyl–4–hydroxycoumarins. Formation of 3–phenylacetic acid benzisoxazole from 3–phenyl–4–hydroxycoumarin and hydroxylamine hydrochloride"; Chemical Abstracts XP002157558 (1989).

Nakata, et al; "Degree–of–freedom effect in three consecutive mass spectral fragmentations"; Chemical Abstracts XP002157559 (1973).

Benoit–Guyod, et al; "Analgesic and antipyretic derivatives of dipropylacetic acid"; Chemical Abstracts XP002157560 (1967).

Eberson et al; "Palladium (II) Catalyzed Aromatic Acetoxylation. II. Nuclear Acetoxylation of Aromatic Compounds. Reversal of the Usual Isomer Distribution Pattern in Aromatic Substitution"; Chemical Abstracts XP002157561 (1973).

Derwent Publications; XP002157564; Aug. 18, 1994 (WO 94 18188).

Ziegler; "4–hydroxycoumarin"; Chemical Abstracts XP002157555.

*Primary Examiner*—Paul J. Killos
(74) *Attorney, Agent, or Firm*—Sughrue Mion, PLLC

(57) ABSTRACT

The present invention provides a salicylic acid ester derivative having an impurity content lower than a specific level and expressed by the following formula (1)

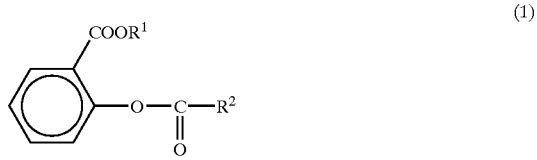

(1)

(in the formula, $R^1$ is methyl group or ethyl group, $R^2$, which may be substituted optionally, is an alkyl group having a carbon number of from 1 to 30, alkoxy group having a carbon number of from 1 to 30, aryl group having a carbon number of from 6 to 30, aryloxy group having a carbon number of from 6 to 30, aralkyl group having a carbon number of from 6 to 30 or aralkyloxy group having a carbon number of from 6 to 30). The salicylic acid ester derivative is effective as a terminal blocking agent or a polymerization promoting agent for a polycarbonate, and gives a polycarbonate having good color tone and suitable for optical material use.

69 Claims, No Drawings

SALICYLIC ACID ESTER DERIVATIVE AND ITS PRODUCTION

TECHNICAL FIELD

The present invention relates to a salicylic acid ester derivative having an impurity concentration not more than a specific level and its production process, more particularly, the present invention relates to a salicylic acid ester derivative having a quality and a reactivity sufficiently high to be usable as a terminal blocking agent or a polymerization promoter in the production process of an aromatic polycarbonate and to its production process.

An aromatic polycarbonate especially useful for optical materials can be produced by the use of the salicylic acid ester derivative disclosed in the present invention. The aromatic polycarbonate produced by using the derivative is preferable especially for optical disks among the optical materials.

BACKGROUND ARTS

Polycarbonates are widely used owing to the excellent mechanical properties such as impact resistance as well as heat-resistance, transparency, etc. Especially, a polycarbonate having bisphenol A (2,2-bis(4-hydroxyphenyl)propane) as a repeating unit is recently increasing its demand mainly in the optical media use such as compact disk and CD-ROM.

The coupling reaction of an aromatic diol such as bisphenol A with phosgene (interfacial polymerization process), the transesterification reaction of an aromatic diol with a diaryl carbonate such as diphenyl carbonate in molten state (melt process), etc., are known as the process for the production of the polycarbonate.

Among the production processes, the melt process is expected to be promising in future compared with interfacial polymerization process because the melt process is free from the problem of the use of toxic phosgene and halogen compounds such as methylene chloride as a solvent to enable the production of polycarbonate at a low cost.

There are several disclosed examples to improve the physical properties of polycarbonate produced by the melt process by controlling the structure of the terminal group of the polymer.

For example, JP-B 7-39483 (hereunder, JP-B means "Japanese Examined Patent Publication") and JP-A 6-157739 (hereunder, JP-A means "Japanese Unexamined Patent Publication") describe the blocking of the terminal groups with specific compounds expressed by the following formula (a carbonic acid diester having a carbon number of from 17 to 50)

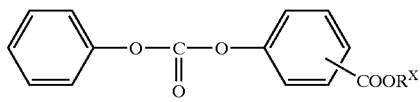

[$R^X$ is a hydrocarbon group having a carbon number of from 3 to 36] or the following formula

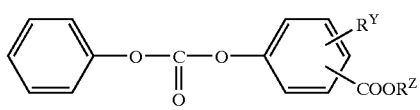

[$R^Y$ is a hydrocarbon group having a carbon number of from 1 to 30, and $R^Z$ is a hydrocarbon group having a carbon number of from 1 to 20]. However, the terminal blocking agents disclosed in the above specifications have defects which its reaction needs long time, etc., and there is no disclosure of the influence of impurity concentration in the blocking agent on the terminal blocking reaction rate and the color of the produced polymer in the case of using the above compound as the terminal blocking agent.

The inventors of the present invention have disclosed in JP-A 10-36497 and U.S. Pat. No. 5,696,222, etc., that a specific carbonic acid diester derivative containing a salicylic acid ester derivative as an eliminable group in the constituent component is effective as a terminal blocking agent in the process for the production of polycarbonate by melt process. However, the influence of impurities in these specific carbonic acid diester derivatives on the polymer and the influence of impurities on the production of the derivative were left unexamined in the above specifications.

A carbonic acid diester compound can be synthesized generally by a known method, as disclosed in JP-A 52-111540 for example, comprising the coupling of a chloroformate expressed by the following general formula

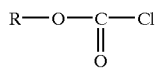

(R is phenyl or benzyl) with an alcohol expressed by the following formula

(R is an alkyl) in the presence of a base such as an amine.

Since the raw materials contains large amounts of chlorine and nitrogen, chlorine and nitrogen impurities may be included in the carbonic acid diester synthesized by this process according to the synthetic conditions and purification method.

The use of such carbonic acid diester containing large amount of impurities as the terminal blocking agent of a polycarbonate creates various problems such as the insufficient progress of the reaction and the deterioration of the color of the produced polymer. However, the means for solving these problems are left uninvestigated.

Problems to be Solved by the Invention

The object of the present invention is to produce a polycarbonate having good color and suitable for optical materials, especially for optical disk substrate without lowering the terminal blocking reaction rate or the polymerization promoting reaction rate in the case of using a specific salicylic acid ester derivative as a terminal blocking agent or a polymerization promoter by decreasing the impurity content of the salicylic acid ester derivative effective as a terminal blocking agent or a polymerization promoting agent of polycarbonate to or below a specific level.

Means for Solving the Problems

The present invention discloses a specific salicylic acid ester derivative effective as a terminal blocking agent or a polymerization promoting agent of a polycarbonate and having an impurity concentration decreased to or below a specific level.

Salicylic Acid Ester Derivative

The specific salicylic acid ester derivative compound in the present invention means a compound expressed by the following formula (1)

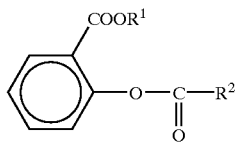
(1)

(wherein R¹ is methyl or ethyl, R² is an alkyl group having a carbon number of from 1 to 30, an alkoxy group having a carbon number of from 1 to 30, an aryl group having a carbon number of from 6 to 30, an aryloxy group having a carbon number of from 6 to 30, an aralkyl group having a carbon number of from 6 to 30 or an aralkyloxy group having a carbon number of from 6 to 30. The group R² may have, as a substituent, methoxycarbonyl group, ethoxycarbonyl group, 2-(methoxycarbonyl)-phenyloxycarbonyl group, 2-(methoxycarbonyl)phenyloxycarbonyloxy group, 2-(ethoxycarbonyl)phenyloxycarbonyl group, 2-(ethoxycarbonyl)-phenyloxycarbonyloxy group or an aryloxycarbonyl group or an aralkyloxycarbonyl group having a carbon number of from 6 to 10).

The alkyl group having a carbon number of from 1 to 30 may have straight-chain form, branched form or cyclic form and may contain unsaturated group. Examples of such alkyl groups are straight-chain alkyl groups such as methyl group, ethyl group, n-propyl group, n-butyl group, n-pentyl group, n-hexyl group, n-octyl group, n-nonyl group, n-lauryl group, n-stearyl group, n-docosanyl group and n-heptacosanyl group, branched-chain alkyl groups such as isopropyl group, t-butyl group, 3-hexyldecanyl group and 6-butyltetracosanyl group, unsaturated alkyl groups such as allyl group, butenyl group, pentenyl group, hexenyl group, dodecenyl group, oleyl group and 6-docosenyl group, cyclic alkyl groups such as cyclohexyl group, 4-nonylcyclohexyl group, 4-pentenylcyclohexyl group and norbornyl group, etc.

The alkoxy groups having a carbon number of from 1 to 30 may have straight-chain form, branched form or cyclic form and may contain unsaturated group. Examples of such alkoxy groups are straight-chain alkoxy groups such as methoxy group, ethoxy group, n-propoxy group, n-butoxy group, n-hexyloxy group, n-octyloxy group, n-nonyloxy group, n-stearyloxy group, n-docosanyloxy group and n-hexacosanyloxy group, branched-chain alkoxy groups such as isopropyloxy group and 3-hexyldodecanyloxy group, unsaturated alkoxy groups such as allyloxy group, butenyloxy group, pentenyloxy group, hexenyloxy group and dodecenyloxy group, cyclic alkyloxy groups such as cyclohexyloxy group, etc.

The aryl group having a carbon number of from 6 to 30 are, for example, phenyl group, naphthyl group, anthranyl group, biphenyl group and pyrenyl group.

Examples of the aryloxy groups having a carbon number of from 6 to 30 are phenyloxy group, naphthyloxy group, anthranyloxy group, biphenyloxy group and pyrenyloxy group.

The aralkyl groups having a carbon number of from 6 to 30 are, for example, alkyl groups, which have an aryl-substituent, such as benzyl group, 4-phenylbutyl group, 2,2-diphenylpropyl group, 10-naphthyldecanyl group, 3-phenyltetracosanyl group, 4-phenyl-2-dodecenyl group and 3,5-diphenylcyclohexyl group, aryl groups, which have an alkyl-substituent, such as 6-propylnaphthyl group, 2,4-dinonylphenyl group, 6-butylanthranyl group, 4-octylbiphenyl group, 4-cyclohexylphenyl group, 3,5-dihexenylphenyl group and 2-t-butylphenyl group, aralkyl groups such as 4-cumylphenyl group and 2,4-dimethyl-4-cumylphenyl group, etc.

The aralkyloxy groups having a carbon number of from 6 to 30 are, for example, alkyloxy groups, which have an aryl-substituent, such as benzyloxy group, 4-phenylbutyloxy group, 2,2-diphenylpropyloxy group, 10-naphthyldecanyloxy group, 3-phenyltetracosanyloxy group, 4-phenyl-2-dodecenyloxy group and 3,5-diphenylcyclohexyloxy group, aryloxy groups, which have an alkyl-substituent, such as 6-propylnaphthyloxy group, 2,4-dinonylphenyloxy group, 6-butylanthranyloxy group, 4-octylbiphenyloxy group, 4-cyclohexylphenyloxy group, 3,5-dihexenylphenyloxy group and 2-t-butylphenyloxy group, aralkyloxy groups such as 4-cumylphenyloxy group and 2,4-dimethyl-4-cumylphenyloxy group, etc.

The above alkyl groups, alkoxy groups, aryl groups, aryloxy groups, aralkyl groups and aralkyloxy groups may have methoxy carbonyl group, ethoxy carbonyl group, 2-(methoxycarbonyl)phenyloxycarbonyl group expressed by the following formula,

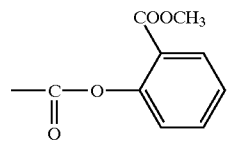

2-(methoxycarbonyl)phenyloxycarbonyloxy group expressed by the following formula,

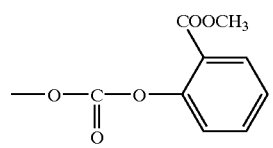

2-(ethoxycarbonyl)phenyloxycarbonyl group expressed by the following formula,

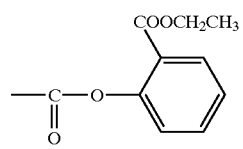

2-(ethoxycarbonyl)phenyloxycarbonyloxy group expressed by the following formula,

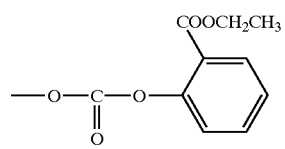

or an aryloxycarbonyl group or aralkyloxycarbonyl group having a carbon number of from 6 to 10 and expressed by the following formula

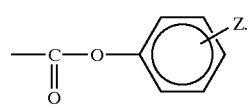

(wherein Z is hydrogen atom or an alkyl group having a carbon number of from 1 to 4) as a substituent group.

The alkyl groups having a carbon number of from 1 to 4 and expressed by the symbol Z mean methyl group, ethyl group, n-propyl group, i-propyl group, n-butyl group, sec-butyl group and t-butyl group.

Concrete examples of these salicylic acid ester derivatives are 2-methyloxycarbonylphenyl-methyl carbonate, 2-methyloxycarbonylphenyl-n-butyl carbonate, 2-methyloxycarbonylphenyl-n-hexyl carbonate, 2-ethyloxycarbonylphenyl-n-nonyl carbonate, 2-methyoxycarbonylphenyl-n-stearyl carbonate, 2-methyloxycarbonylphenyl-n-octacosanyl carbonate, 2-methyloxycarbonylphenyl-phenyl carbonate, 2-ethyloxycarbonylphenyl-phenyl carbonate, 2-methyloxycarbonylphenyl-p-t-butylphenyl carbonate, 2-ethyloxycarbonylphenyl-p-t-butylphenyl carbonate, 2-methyloxycarbonylphenyl-naphthyl carbonate, 2-ethyloxycarbonylphenyl-biphenyl carbonate, 2-methyloxycarbonylphenyl-pyrenyl carbonate, 2-methyloxycarbonylphenyl-p-cumylphenyl carbonate, 2-ethyloxycarbonylphenyl-p-cumylphenyl carbonate, bis(2-methyloxycarbonylphenyl) carbonate, 2-methyloxycarbonylphenyl acetate, 2-methyloxycarbonylphenyl n-butyrate, 2-methyloxycarbonylphenyl n-hexylate, 2-ethyloxycarbonylphenyl n-nonylate, 2-methyloxycarbonylphenyl n-stearate, bis(2-methyloxycarbonylphenyl) terephthalate, bis(2-methyloxycarbonylphenyl) isophthalate, bis(2-ethyloxycarbonylphenyl) terephthalate, bis(2-ethyloxycarbonylphenyl) isophthalate, bis(2-methyloxycarbonylphenyl) succinate, bis(2-ethyloxycarbonylphenyl) adipate, 1,4-butanediol bis(2-ethyloxycarbonylphenyl) carbonate and 1,10-decanediol bis(2-ethyloxycarbonylphenyl) carbonate.

Impurities in Salicylic Acid Ester Derivative

The present invention is characterized in that the impurity content of the salicylic acid ester derivative expressed by the above formula (1) is a specific level or below.

The salicylic acid ester derivative disclosed in the present invention is especially useful as a terminal blocking agent for polycarbonate, and it has been found that, in the case of using the derivative as a terminal blocking agent, the impurity in the blocking agent has especially large influence on the polymer quality because the terminal is blocked by adding at most 3 to 5% by weight of the agent based on 100 parts by weight of the polymer.

The present invention is characterized by the use of the salicylic acid ester derivative expressed by the above formula (1) having a chlorine content of a specific level or below.

The chlorine content is concretely 100 ppm or below, preferably 30 ppm or below and more preferably 10 ppm or below. When a salicylic acid ester derivative having a chlorine content higher than the above limit is used as a terminal blocking agent for polycarbonate, the terminal blocking reaction rate is significantly lowered and a polymer having undesirable color is produced.

The chlorine content of the raw material can be determined by elementary analysis. A preferable example of the analytic method is Dorman's microamperometric titration method.

The chlorine contamination is especially liable to occur when a phosgene, an acid halide or a halogenated formic acid ester is used as the synthetic raw material. Unreacted chlorine and free chlorine ion can be removed by washing, etc., after the synthesis of the above salicylic acid ester derivative mainly by chemical reaction, and concretely, these contaminants are effectively removed by the following method.

Examples of the methods for decreasing chlorine content in the above salicylic acid ester derivative are a method to wash the derivative with hot water several times, a method to dissolve the salicylic acid ester derivative in a water-immiscible organic solvent and wash the solution with a neutral or basic aqueous solution, a method to remove the chlorine by using a chlorine-adsorbent such as hydrotalcite, and a method to adsorb the chlorine by ion-exchange resin.

The above salicylic acid ester derivative preferably has a nitrogen content of a specific level or below. The nitrogen content is preferably 100 ppm or below, more preferably 30 ppm or below and especially 10 ppm or below. Color of polymer is deteriorated by the use of a salicylic acid ester derivative having a nitrogen content exceeding the above level as a terminal blocking agent for polycarbonate.

The nitrogen content in the salicylic acid ester derivative can be decreased, for example, by washing the derivative with a neutral water (hot water), washing with an acidic aqueous solution having a pH of 6 or below, or removing with an acidic ion exchange resin.

The total content of metallic elements in the above salicylic acid ester derivative is preferably 30 ppm or below. The metallic element means alkali metals such as sodium and potassium, iron, chromium, manganese, nickel, etc. The content of the metal can be determined by atomic absorption analysis, plasma ion emission spectrometry (ICP), etc.

Preferable content of metal is 10 ppm or below, more preferably 5 ppm or below and especially 2 ppm or below. When the metal content exceeds the above level, a disproportionation reaction may take place in the heating and melting stage for the reaction of the above salicylic acid ester derivative, deteriorate the color of the polymer or inhibit the terminal blocking reaction. The disproportionation reaction means the variation of the chemical structure of the salicylic acid ester derivative according to the following reaction scheme.

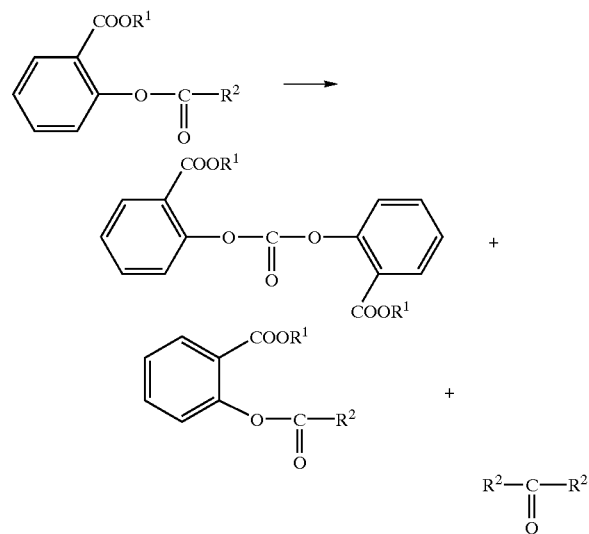

The content of metal in the above salicylic acid ester derivative can be decreased by removing the metal e.g. by washing with neutral water (hot water) or by using a compound capable of forming a complex with the metal ion such as ethylenediaminetetraacetic acid, oxalic acid, citric acid or bipyridine, a metal-adsorbing polymer such as ion exchange resin, polyallylamine, chitosan, polyacrylic acid, polyvinyl alcohol or alginic acid, a metal-clathrating compound such as crown ether, etc.

Since there are variations in the kind and quantity of the metal removable by the same metal removing process, the process can be arbitrarily selected according to the objective metal to be removed, and there is no particular restriction on the combination of the above methods to achieve the object of the present invention.

Production Reaction 1 of Salicylic Acid Ester Derivative

An example of the reaction for producing these salicylic acid ester derivatives of the present invention is the reaction of phosgenes, an acid halide compound or a halogenated formic acid ester expressed by the following formulas (2), (3) or (4)

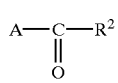
(2)

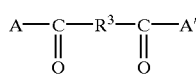
(3)

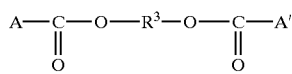
(4)

(wherein A and A' are each a halogen; $R^3$ is a bivalent arylene group or aralkylene group having a carbon number of from 1 to 30) with a salicylic acid ester expressed by the following formula (5)

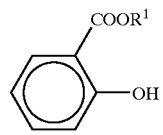
(5)

in the presence of a basic compound.

The term phosgenes means phosgene (Cl—CO—Cl), phosgene dimer (Cl—CO—O—CCl$_3$) and phosgene trimer (CCl$_3$—O—CO—O—CCl$_3$).

When the above halogen compound (phosgenes, acid halide compound or halogenated formic acid ester) is left in the system in unreacted state, the chlorine-contamination probability of the produced salicylic acid ester derivative becomes high and, accordingly, prevention of the residual unreacted halogen compound in the reaction stage is effective for decreasing the chlorine content. It can be effectively achieved by using the salicylic acid ester of the formula (5) and/or the basic compound in excess of the above halogen compound.

Impurity in Raw Material in the Production Reaction 1 of Salicylic Acid Ester Derivative The sum of the metallic elements included in the phosgenes, the acid halide compound or halogenated formic acid ester expressed by the above formulas (2) to (4) and the salicylic acid ester expressed by the above formula (5) is preferably 100 ppm or below. The use of raw materials having a metallic element content higher than the above limit lowers the reaction yield and increases the metal contamination risk of the produced salicylic acid ester derivative.

Reaction Condition of the Production Reaction 1 of Salicylic Acid Ester Derivative Any known basic compound usable for the reaction of general acid halide with hydroxyl group can be used without restriction as the basic compound in the above production reaction, however, it is preferable to use an alkali metal compound such as sodium hydroxide, potassium hydroxide, sodium bicarbonate and sodium carbonate, an alkaline earth metal compound such as calcium hydroxide or an amine such as pyridine, trimethylamine, triethylamine, piperidine, dimethylaminopyridine, tetramethylammonium hydroxide, ethanolamine, ethylenediamine and polyallylamine.

The kind of solvent to be used in the above production reaction has no particular limitation, however, it is preferable to use a general-purpose organic solvent such as dichloromethane, xylene, toluene and tetrahydrofuran or a double-layer solvent system composed of the above solvent and water. A catalyst such as tetramethylammonium chloride may be used for proceeding the reaction in high efficiency. The reaction is carried out usually at 100° C. or below, preferably at room temperature or below. There is no particular restriction on the reaction apparatus and the like. The product is subjected to the above purification (washing) operation and further purified by distillation or recrystallization to keep the objective low impurity content after the completion of the reaction.

Production Reactions 2 and 3 of Salicylic Acid Ester Derivative

The following production reactions 2 and 3 can be used in addition to the above-mentioned production reaction 1 when the salicylic acid ester derivative is expressed by the following formula (1)-2

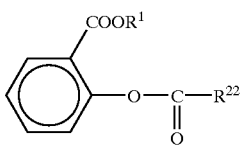
(1)-2

(in the formula (1)-2, $R^1$ is methyl group or ethyl group, $R^{22}$ is an aryl group having a carbon number of from 6 to 30, an aryloxy group having a carbon number of from 6 to 30, an aralkyl group having a carbon number of from 6 to 30 or an aralkyloxy group having a carbon number of from 6 to 30. $R^{22}$ group may have, as a substituent, methoxycarbonyl group, ethoxycarbonyl group, 2-(methoycarbonyl) phenyloxycarbonyl group, 2-(methoxy-carbonyl) phenyloxycarbonyloxy group, 2-(ethoxycarbonyl) phenyloxy-carbonyl group, 2-(ethoxycarbonyl) phenyloxycarbonyloxy group or an aryloxycarbonyl group or aralkyloxycarbonyl group having a carbon number of from 6 to 10).

The production reaction 2 comprises the production of a salicylic acid ester derivative from an aromatic ester derivative expressed by the following formula (6)

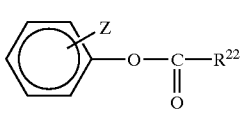
(6)

(in the formula, Z groups are same or different groups selected from hydrogen atom and an alkyl group having a carbon number of from 1 to 4, and $R^{22}$ is same as defined in the above formula (1)-2) and a salicylic acid ester expressed by the following formula (5)

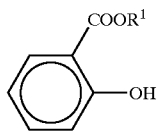

(5)

(in the formula, $R^1$ is methyl group or ethyl group) in the presence of a catalyst.

The production reaction 3 comprises the production of a salicylic acid ester derivative from an aromatic ester derivative of the following formula (6)-2

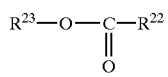

(6)-2

(in the formula, $R^{22}$ is same as defined in the above formula (1)-2, and $R^{23}$ is an aryl group having a carbon number of from 1 to 30 or an aralkyl group having a carbon number of from 1 to 30) and an aromatic carbonic acid ester of the following formula (7)

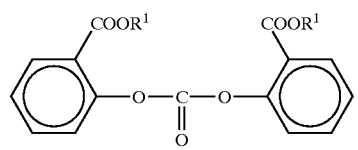

(7)

(in the formula, $R^1$ is methyl group or ethyl group) in the presence of a catalyst.

Reaction Condition of the Production Reaction 2 of Salicylic Acid Ester Derivative The reaction scheme of the production reaction 2 can be expressed as follows.

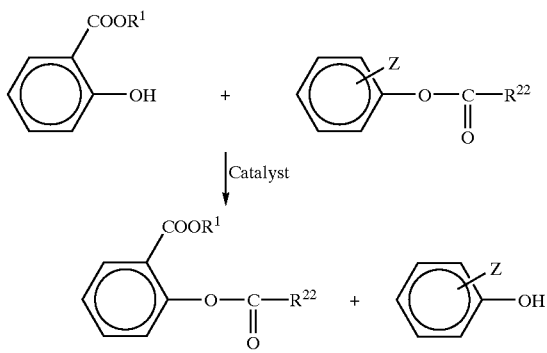

(11)

Salicylic acid ester derivative can be produced as a liquid mixture of two or more kinds of compounds. For example, in the case of a compound wherein $R^{22}$ is phenyloxy group, the product is composed of two kinds of compounds consisting of a compound having a $COOR^1$ group as substituent to the ortho-position of the phenyl group and a compound free from the substituent. These salicylic acid ester derivatives can be separated by distillation or the like.

In the above reaction, it is preferable to keep the concentration of the produced aromatic monohydroxy compound expressed by the formula (11) in the above reaction scheme in the reactor as low as possible to rapidly proceed the reaction and suppress the undesirable side reactions. Concretely, the concentration of the produced aromatic monohydroxy compound of the formula (11) in the reaction liquid is maintained to preferably 2% or below, more preferably 1% or below. The presence of the aromatic monohydroxy compound at a concentration higher than the above limit induces a side reaction to form products other than the objective substance and sometimes retards the reaction.

The reaction under reduced pressure is preferable to suppress the concentration of the aromatic monohydroxy compound of the formula (11). More preferably, the reaction is carried out under a temperature and pressure condition to enable the distillation and recovery of the aromatic monohydroxy compound of the formula (11). The range of the reaction temperature is preferably 100 to 300° C., more preferably 150 to 280° C., and especially preferably 170 to 260° C., and the evacuation condition is preferably 600 torr or below, more preferably 500 to 1 torr, especially preferably 400 to 10 torr.

Reaction Condition of the Production Reaction 3 of Salicylic Acid Ester Derivative The reaction scheme of the production reaction 3 can be expressed as follows.

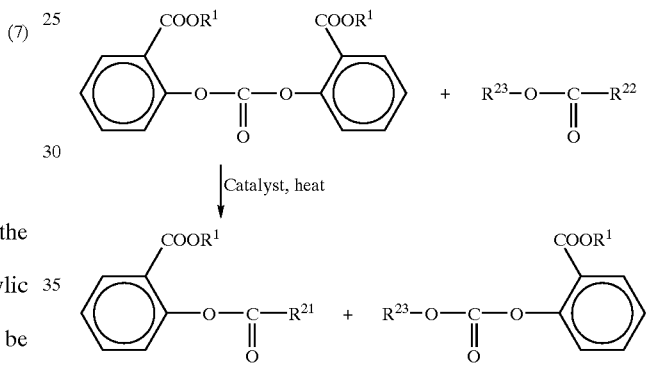

The above reaction scheme shows that the product is a liquid mixture of two or more kinds of salicylic acid ester derivatives, and these aromatic carbonic acid diesters can be separated by a process such as distillation.

It is necessary that all raw materials are in molten state in the reaction, and the reaction temperature is preferably from 100 to 300° C., more preferably from 120 to 280° C., especially from 140 to 260° C. and the temperature can be adjusted according to the melting points and boiling points of the raw materials and the objective compound. The reaction may be carried out under atmospheric pressure, however, it is preferably performed in nitrogen-substituted atmosphere in the range of normal pressure to 133.32 hPa (100 torr).

Impurities in Raw Materials of the Production Reactions 2 and 3 of Salicylic Acid Ester Derivative In the production reactions 2 and 3, the chlorine content of the salicylic acid ester expressed by the above formula (5), the aromatic ester derivative expressed by the above formula (6) or (6)-2 and the aromatic carbonic acid ester expressed by the above formula (7) is preferably 100 ppm or below each. The chlorine content is preferably 20 ppm or below, more preferably from 10 to 0.1 ppm. Chlorine content exceeding 100 ppm exerts adverse effect on the activity of catalyst used in the reaction to decrease the reaction activity to an undesirable level.

Even if the chlorine content of a raw material is not more than 100 ppm, bad effect is exerted on the activity of the catalyst used in the reaction to decrease the reaction activity when the other raw material has a chlorine content of 100 ppm or above. Accordingly, it is necessary that both raw materials have chlorine contents of 100 ppm or below.

There is no particular restriction on the method for decreasing the chlorine contents of the above raw materials to 100 ppm or below, however, washing with hot water, treatment with an adsorbent such as hydrotalcite and purification by distillation are exemplified as concrete decreasing methods. Two or more of the above methods may be combined with each other such as the distillation after the treatment with a chlorine adsorbent.

The chlorine content of the raw material can be determined by elementary analysis. A preferable example of the analytic method is Dorman's microamperometric titration method.

The total content of metals in each of the above salicylic acid ester expressed by the above formula (5), the aromatic ester derivative expressed by the above formula (6) or (6)-2 and the aromatic carbonic acid ester expressed by the above formula (7) is preferably 50 ppm or below. The term "metals" means alkali metals, iron, copper, lead, chromium, nickel, manganese, cobalt, etc. The total content is more preferably 20 ppm or below, especially 10 ppm or below. When the metal content is higher than the above level, the activity of the catalyst to be used in the reaction is lowered and undesirable side reactions take place.

Even if the content of metal in a raw material is not more than 50 ppm, bad effect is exerted on the activity of the catalyst used in the reaction to remarkably decrease the reaction activity when the other raw material has a metal content of 50 ppm or above. Accordingly, it is preferable that both raw materials have metal contents of 50 ppm or below.

There is no particular restriction on the method for decreasing the metal contents of the above raw materials to 50 ppm or below, however, washing with hot water, treatment with an adsorbent such as ion exchange resin and purification by distillation are exemplified as concrete decreasing methods. Two or more of the above methods may be combined with each other such as the distillation after the washing with hot water.

Impurities in Raw Materials in the Production Reactions 1 to 3 of Salicylic Acid Ester Derivative In the above three kinds of reactions for producing a salicylic acid ester derivative, the amounts of water in the phosgenes, the acid halide or the halogenated formic acid esters expressed by the above formulas (2) to (4), the salicylic acid esters expressed by the above formula (5), the aromatic ester derivatives expressed by the above formula (6) or (6)-2 and the aromatic carbonic acid esters expressed by the above formula (7) are preferably not more than 5% by weight each. The water content is more preferably not more than 4% by weight, especially 1 to 0.01% by weight. Side reactions such as the hydrolysis of the salicylic acid ester and carbonic acid diester used as the raw materials may take place when the water content is higher than the above level.

There is no particular restriction on the method for decreasing the water contents of the above raw materials to 5% by weight or below, however, purification by distillation, drying with heat, drying under reduced pressure and the use of desiccant such as anhydrous magnesium sulfate are exemplified as concrete decreasing methods. Two or more of the above methods may be combined with each other such as the distillation after the adsorption of water with a desiccant.

In the above three kinds of reactions for producing the salicylic acid ester derivative, the amount of aromatic hydroxy compound in the phosgenes, the acid halides or halogenated formic acid esters expressed by the above formulas (2) to (4), the salicylic acid esters expressed by the above formula (5), the aromatic ester derivatives expressed by the above formula (6) or (6)-2 and the aromatic carbonic acid esters expressed by the above formula (7) are not more than 3% by weight each.

The aromatic hydroxy compound means an aromatic hydroxy compound expressed by the following formula (12) or (13)

(in the formula, Xa is an alkyl group having a carbon number of from 1 to 30, an aryl group having a carbon number of from 1 to 30 or an aralkyl group having a carbon number of from 6 to 30, which may have, as a substituent, methoxycarbonyl group, ethoxycarbonyl group, 2-(methoxycarbonyl)phenyloxycarbonyl group, 2-(methoxycarbonyl)phenyloxycarbonyloxy group, 2-(ethoxycarbonyl)phenyloxycarbonyl group, 2-(ethoxycarbonyl)phenyloxycarbonyloxy group or an aryloxycarbonyl group or aralkyloxycarbonyl group having a carbon number of from 6 to 10),

(in the formula, Y is a bivalent alkylene group having a carbon number of from 1 to 30, an arylene group or an aralkylene group) or an aromatic hydroxy compound existing in the salicylic acid ester of the above formula (5) as an impurity.

Concrete examples of the aromatic hydroxy compound existing in the salicylic acid ester of the formula (5) as an impurity are phenol, o-cresol, m-cresol, p-cresol, methyl p-hydroxybenzoate and ethyl p-hydroxybenzoate.

The content of the aromatic monohydroxy compound is preferably not more than 3% by weight, more preferably not more than 2% by weight and especially 1.0 to 0.01% by weight.

There is no particular restriction on the method for decreasing the content of the aromatic monohydroxy compound in the above raw materials to 3% by weight or below, however, purification by distillation, recrystallization and the treatment with an adsorbent such as a laminar clay mineral before the synthesis of the objective salicylic acid ester compound of the present invention are exemplified as concrete decreasing methods. Two or more of the above methods may be combined with each other such as recrystallization after distillation. Although there is no particular restriction on the kind of solvent for recrystallization, solvent such as xylene is preferably used for recrystallization.

Catalyst for the Production Reactions 2 and 3 of the Salicylic Acid Ester Derivative Any known transesterification catalysts can be used in the scope of the present invention as the catalyst for the reactions (production reactions 2 and 3) for producing the salicylic acid ester derivative expressed by the above formula (1)-2 and preferable catalysts are compounds of alkali metals, alkaline earth metals, and the group 3 and group 12 elements of the periodic table.

The alkali metal compounds are, concretely, metallic lithium, sodium or potassium, their hydroxides, inorganic acid salts such as hydrochlorides, carbonates, nitrates or sulfates, organic acid salts such as carboxylic acid salts and alkoxides such as alcoholates and phenolates.

The alkaline earth metal compounds are, concretely, metallic beryllium, magnesium, calcium or strontium, their hydroxides, oxides, inorganic salts such as hydrochlorides, carbonates, nitrates or sulfates, organic acid salts such as carboxylic acid salts and alkoxides such as alcoholates and phenolates.

The compounds of the group 3 elements of the periodic table are, concretely, metallic lanthanoid elements such as scandium, yttrium and lanthanum, actinoid elements, their hydroxides, oxides, inorganic acid salts such as hydrochlorides, carbonates, nitrates or sulfates, organic acid salts such as carboxylic acid salts and alkoxides such as alcoholates and phenolates.

The compounds of the group 12 elements of the periodic table are, concretely, zinc hydroxide, oxide, inorganic acid salts such as hydrochloride, carbonate, nitrate or sulfate, organic acid salts such as carboxylic acid salts and alkoxides such as alcoholate and phenolates.

Especially preferable compounds among the above examples are calcium oxide, lanthanum oxide, lanthanum alkoxides and zinc carboxylates.

Examples of lanthanum alkoxides are aliphatic alkoxylanthanum such as lanthanum trimethoxide, lanthanum triethoxide, lanthanum tripropoxide, lanthanum tricetyloxide, lanthanum tristearyloxide and lanthanum tribehenyloxide and aromatic alkoxylanthanum such as lanthanum triphenoxide, and the examples of zinc carboxylates are zinc acetate, zinc propionate, zinc stearate, zinc behenate, zinc oxalate, zinc sebacate and zinc ascorbate.

Lanthanum oxide is most preferable as the catalyst. However, it is already known that lanthanum oxide is degraded to lanthanum dioxide, etc., by the adsorption of carbon dioxide, water, etc., when left in air and the use of the degraded lanthanum oxide in the reaction is found to cause the lowering of the catalytic activity and the deterioration of the reaction selectivity. The inventors of the present invention have found that the above problems are solved and desirable catalytic activity can be attained by heating lanthanum oxide to remove the adsorbed gaseous components. The lanthanum oxide to be used as a catalyst in the present invention preferably has a weight reduction at 500° C. (reduction of weight caused by the release of adsorbed gaseous components) of 3% by weight or less, and lanthanum oxide of the above quality can be obtained by baking the lanthanum oxide usually at 400° C. or above, preferably at 500° C. to 1500° C.

The above catalyst may be used singly or in combination. The addition timings of the catalysts may be staggered in case of using two or more catalysts, and there is no particular restriction on the use of these catalysts. The amount of the catalyst is preferably $1 \times 10^{-6}$ to $1 \times 10^{-2}$ equivalent of each metal atom based on 1 mol of the salicylic acid ester used as a raw material. The ratio is more preferably $1 \times 10^{-5}$ to $1 \times 10^{-3}$ equivalent and especially $5 \times 10^{-5}$ to $5 \times 10^{-4}$ equivalent on the same basis.

Nitrogen-containing basic compounds are also used as preferable catalysts in the present invention. Examples of the nitrogen-containing basic compounds are ammonium hydroxides having alkyl, aryl or aralkyl group or the like such as tetramethylammonium hydroxide ($Me_4NOH$), tetraethylammonium hydroxide ($Et_4NOH$), tetrabutylammonium hydroxide ($Bu_4NOH$), benzyltrimethylammonium hydroxide ($\phi$"–" $CH_2(Me)_3NOH$) and hexadecyltrimethylammonium hydroxide, tertiary amines such as triethylamine, tributylamine, dimethylbenzylamine and hexadecyldimethylamine, or basic salts such as tetramethylammonium borohydride ($Me_4NBH_4$), tetrabutylammonium borohydride ($Bu_4NBH_4$), tetrabutylammonium tetraphenylborate ($Bu_4NBPh_4$) and tetramethylammonium tetraphenylborate ($Me_4NBPh_4$).

$Me_4NOH$ is preferable among the above examples, and the amount of the nitrogen-containing basic compound is preferably $1 \times 10^{-6}$ to $1 \times 10^{-2}$ equivalent of the ammoniacal nitrogen atom based on 1 mol of the salicylic acid ester used as a raw material. The ratio is more preferably $1 \times 10^{-5}$ to $1 \times 10^{-3}$ equivalent and especially $5 \times 10^{-5}$ to $5 \times 10^{-4}$ equivalent on the same basis. These nitrogen-containing basic compound catalysts may be used singly or in combination. These catalysts may be used in combination with a compound selected from the group of the aforementioned metal catalysts (oxides, alkoxides, hydroxides and carboxylic acid salts of the group 1, group 2, group 3 and/or group 12 elements of the periodic table), and there is no particular restriction on the use of these catalysts.

Deactivation and Neutralization After the Synthesis of Salicylic Acid Ester Derivative The basic compound left after the completion of the above production reaction 1 is preferably neutralized by the addition of at least one kind of compound selected from acidic compounds comprising inorganic acidic compounds and organic sulfonic acid compounds, salts of said acidic compounds and derivatives of said acidic compounds.

In the above production reactions 2 and 3, the catalysts are preferably deactivated after completing the reactions by adding at least one kind of compound selected from acidic compounds comprising inorganic acidic compounds and organic sulfonic acid compounds, salts of said acidic compounds and derivatives of said acidic compounds.

When the produced salicylic acid ester derivative is purified by distillation in the production of the salicylic acid ester derivative without neutralizing the residual basic compound or deactivating the catalyst, disproportionation reaction occurs in the salicylic acid ester derivative produced by the synthetic reaction to lower the yield and, accordingly, a prevention measure has to be taken.

The disproportionation reaction means the reaction expressed by the following scheme.

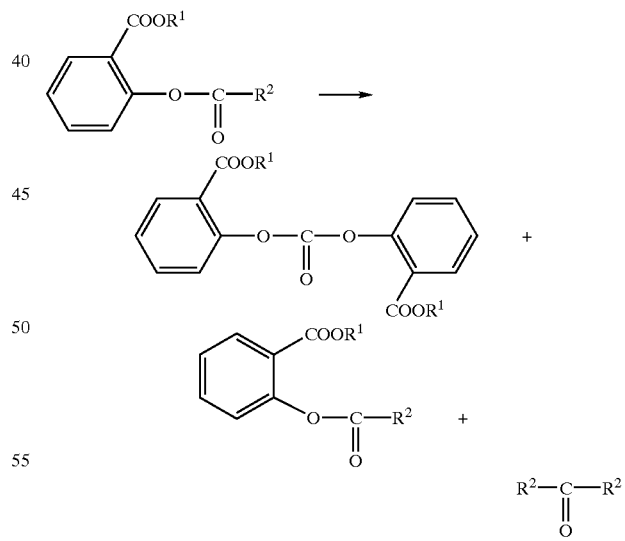

The yield of salicylic acid ester derivative undesirably decreases by the disproportionation reaction. The undesirable disproportionation reaction in the distillation of the produced salicylic acid ester derivative can be suppressed and the salicylic acid ester derivative is produced in high efficiency by adding at least one compound selected from acidic compound derivatives to neutralize the residual basic compound.

Inorganic acids and solid acids are used as the inorganic acidic compounds for the neutralization of the residual basic compound and the deactivation of the catalyst.

The inorganic acid means an inorganic compound capable of giving proton of Broensted's definition, dissociating into proton and counter ion in water at 25° C. and giving a solution having neutral pH or below. Concrete examples of the inorganic acid are phosphoric acid (orthophosphoric acid), sulfuric acid, nitric acid, phosphinic acid, phosphonic acid, diphosphonic acid, hydrochloric acid, pyrophosphoric acid, metaphosphoric acid and nitrous acid. These acids may be used in the form of metal salts, ammonium salts or the like.

The solid acid means an inorganic compound capable of giving proton by the Broensted's definition in spite of taking a solid state, and is concretely zeolites, clay compounds, metal oxides, solid phosphoric acids, heteropolyacids, etc.

Zeolite is a condensed silicate having crystalline aluminosilicate as the principal skeleton and concrete examples of the zeolite are synthetic zeolites such as ZMS-5 ($Na_n$ ($Al_nSi_{96-n}O_{192})_{16}H_2O$ (n<27), zeolite X ($Na_{86}$ ($Al_{86}Si_{106}O_{384})_{264}H_2O$ and zeolite Y ($Na_{56}(Al_{56}Si_{136}O_{384})_{250}H_2O$ and natural zeolites such as mordenite ($Na_8(Al_8Si_{40}O_{96})_{24}H_2O$ and chabazite ($Ca_2$ ($Al_4Si_8O_{24})_{13}H_2O$.

Examples of the clay compounds are kaolin, montmorillonite, talc and acid clay.

Concrete examples of the metal oxides are $TiO_2$, $SiO_2$, $ZrO_2$, $SiO_2$ "$Al_2O_3$, $SiO_2$—$ZrO_2$, $SiO_2$—$MoO_3$, $SiO_2$—$MgO$, $TiO_2$—$Al_2O_3$, $TiO_2$—$SiO_2$, $Al_2O_3$—$MoO_3$ and $Al_2O_3$—$WO_3$.

The solid phosphoric acid is e.g. diphosphorus pentoxide.

Heteropolyacid means an acid formed from two or more kinds of metals, and is concretely $H_3PW_{12}O_{40}$, $H_4SiW_{12}O_{40}$, $H_5PMo_{10}V_2O_{40}$ and $H_3PMo_{12}O_{40}$.

Phosphoric acid, diphosphorus pentoxide, talc and ZMS-5 are preferable among the above inorganic acidic compounds.

Compounds selected from the following general formulas (8), (9) and (10) are concrete examples of the organic sulfonic acid compounds.

The Compound Expressed by the Formula (8)

$$A^1-(Y^1-SO_3X^1)_m \quad (8)$$

In the formula, $A^1$ is an m-valent hydrocarbon group having a carbon number of from 1 to 30, which may have a substituent or not, $Y^1$ is single bond or oxygen atom, $X^1$ is a secondary or tertiary univalent hydrocarbon group or 1 equivalent of metal cation, ammonium cation or phosphonium cation, and m is an integer of from 1 to 4.

The hydrocarbon group $A^1$ is an alkyl group having a carbon number of from 5 to 15 or an aryl group having a carbon number of from 6 to 15, which may have, as a substituent, an alkyl group having a carbon number of from 1 to 15.

The secondary or tertiary univalent hydrocarbon group $X^1$ is preferably a secondary or tertiary alkyl group expressed e.g. by the following formula (8)-a $$-C\begin{matrix}R^3\\R^4\\R^5\end{matrix} \quad (8)\text{-a}$$

[in the formula, $R^3$ and $R^5$ are same or different hydrogen atoms or alkyl groups having a carbon number of from 1 to 5 and $R^4$ is hydrogen atom, phenyl group or an alkyl group having a carbon number of from 1 to 5 provided that two of $R^3$, $R^4$ and $R^5$ are not hydrogen atom at the same time]. Especially preferable groups are those of the formula (8)-a wherein $R^3$ and $R^5$ are same or different hydrogen atoms, methyl groups, ethyl groups or propyl groups and $R^4$ is methyl group or phenyl group.

The one equivalent metal cation is e.g. cation of an alkali metal such as lithium, sodium or potassium, 1/2 of bivalent metal cations or 1/3 of trivalent metal cations, e.g. 1/2 of cations of an alkaline earth metal such as calcium or barium or 1/3 of cations of trivalent metal such as aluminum.

The ammonium cation is for example the cation expressed by the following formula (8)-b $$R^9-\overset{+}{N}\begin{matrix}R^6\\R^7\\R^8\end{matrix} \quad (8)\text{-b}$$

[in the formula, $R^6$, $R^7$, $R^8$ and $R^9$ are each independently hydrogen atom or a univalent hydrocarbon group].

The univalent hydrocarbon groups of the groups $R^6$ to $R^9$, etc., in the formula (8)-b are, for example, alkyl groups having a carbon number of from 1 to 20, aryl groups having a carbon number of from 6 to 10 and aralkyl groups having a carbon number of from 7 to 10.

The phosphonium ion is for example the cation expressed by the following formula (8)-c $$\overset{+}{P}\begin{matrix}R^{10}\\R^{11}\\R^{12}\\R^{13}\end{matrix} \quad (8)\text{-c}$$

[in the formula, $R^{10}$, $R^{11}$, $R^{12}$ and $R^{13}$ are each independently hydrogen atom or a univalent hydrocarbon group].

The univalent hydrocarbon groups of the groups $R^{10}$ to $R^{13}$ in the formula (8)-c are, for example, alkyl groups having a carbon number of from 1 to 20, aryl groups having a carbon number of from 6 to 10 and aralkyl groups having a carbon number of from 7 to 10.

The group $X^1$ is preferably a secondary or tertiary alkyl group, an alkali metal cation, a cation expressed by the above formula (8)-b and a cation expressed by the above formula (8)-c.

The term (m) in the above formula (8) is an integer of from 1 to 4, preferably 1 or 2.

The following compounds are concrete examples of the compounds expressed by the above formula (8).

The exemplified compounds are 2-phenyl-2-propyl dodecyl-benzenesulfonate, 2-phenyl-2-butyl dodecylbenzenesulfonate, octylsulfonic acid tetrabutylphosphonium salt, decylsulfonic acid tetrabutylphosphonium salt, benzenesulfonic acid tetrabutylphosphonium salt, dodecylbenzenesulfonic acid tetraethylphosphonium salt, dodecylbenzenesulfonic acid tetrabutylphosphonium salt, dodecylbenzenesulfonic acid tetrahexylphosphonium salt, dodecylbenzenesulfonic acid tetraoctylphosphonium salt, decylammonium butylsulfate, decylammonium decylsulfate, dodecylammonium methylsulfate, dodecylammonium ethylsulfate, dodecylmethylammonium methylsulfate, dodecyldimethylammonium tetradecylsulfate, tetradecyl-dimethylammonium methylsulfate, tetramethylammonium hexylsulfate, decyltrimethylammonium hexadecylsulfate, tetrabutylammonium dodecylbenzylsulfate, tetraethylammonium dodecylbenzylsulfate and tetramethylammonium dodecylbenzylsulfate.

The Compound Expressed by the Formula (9)

$$^+X^2-A^2-Y^1-SO_3^- \quad (9)$$

[in the formula, $A^2$ is a bivalent hydrocarbon group, $^+X^2$ is a secondary to quaternary ammonium cation or a secondary to quaternary phosphonium cation, and the definition of $Y^1$ is same as the definition in the formula (8)]

In the above formula (9), the bivalent hydrocarbon group $A^2$ is preferably a bivalent saturated aliphatic hydrocarbon group, and an alkylene group having a carbon number of from 1 to 20 is more preferable as the saturated aliphatic hydrocarbon group.

In the formula (9), $^+X^2$ is an ammonium cation or a phoshonium cation. A cation expressed by the following formula (9)-a is preferable as the ammonium cation.

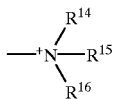
(9)-a

[in the formula, $R^{14}$, $R^{15}$ and $R^{16}$ are each independently hydrogen atom or a univalent hydrocarbon group].

The groups shown as the examples of the groups $R^6$ and $R^7$ of the above formula (1)-b can be used as the examples of the univalent hydrocarbon groups of $R^{14}$ to $R^{16}$. A cation expressed by the following formula (9)-b is preferable as the phosphonium cation.

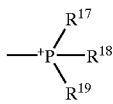
(9)-b

[in the formula, $R^{17}$, $R^{18}$ and $R^{19}$ are each independently hydrogen atom or a univalent hydrocarbon group]. The groups shown as the examples of the groups $R^{10}$ to $R^{13}$ of the above formula (8)-c can be used as the examples of the univalent hydrocarbon groups of $R^{17}$ to $R^{19}$.

The following compounds are concrete examples of the compounds expressed by the above formula (9).

$^-SO_3(CH_2)_3-N^+(CH_3)_3$, $^-SO_3(CH_2)_3-N^+(C_2H_5)_3$, $^-SO_3(CH_2)_3-P^+(C_4H_9)_3$, $^-SO_3(CH_2)_3-P^+(C_6H_5)_3$, $^-SO_3(CH_2)_{15}-N^+(C_2H_5)_3$, $^-SO_3(CH_2)_{15}-P^+(C_6H_5)_3$, $^-SO_3(CH_2)_{15}-P^+(C_4H_9)_3$

The Compound Expressed by the Formula (10)

$$A^3-(^+X^3)_n\cdot(R-Y^1-SO_3^-)_n \quad (10)$$

[in the formula, $A^3$ is an n-valent hydrocarbon group, $^+X^3$ is an ammonium cation or a phosphonium cation, R is a univalent hydrocarbon group, n is an integer of from 2 to 4, and the definition of $Y^1$ is same as the definition in the formula (8)].

Examples of preferable n-valent hydrocarbon groups of $A^3$ are saturated aliphatic hydrocarbon groups such as an alkyl group and an alkylene group having a carbon number of from 1 to 10, aromatic hydrocarbon groups such as an aryl group having a carbon number of from 6 to 10 or saturated aliphatic-aromatic hydrocarbon groups such as an aralkyl group having a carbon number of from 6 to 10.

The ammonium cation and phosphonium cation of $^+X^3$ are e.g. those described in the above formulas (9)-a and (9)-b, respectively.

The group R is a univalent hydrocarbon group and the preferable examples of the group are alkyl groups, aryl groups and aralkyl groups. The carbon numbers of the alkyl group, aryl group and aralkyl group are preferably 1 to 20, 6 to 20 and 7 to 20, respectively.

The term (n) is 2, 3 or 4, and the definition of $Y^1$ is same as above, i.e. single bond or oxygen atom.

The following compounds are concrete examples of the compounds expressed by the above formula (10).

$[(CH_3)_3N^+-(CH_2)_{10}-N^+(CH_3)_3]$.

$[(CH_3)_3N^+-(CH_2)_{10}-N^+(CH_3)_3]$.

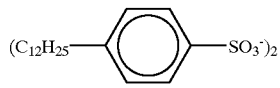

$[(CH_4H_9)_3N^+-(CH_2)_{10}-N^+(CH_4H_9)_3]$.

$[(CH_4H_9)_3N^{30}-(CH_2)_{10}-N^+(C_4H_9)_3]$.

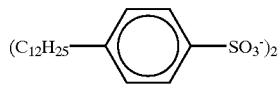

$[(CH_3)_3N^+-(CH_2)_{15}-N^+(CH_3)_3]\cdot(C_{15}H_{31}-SO_4^-)_2$ $[(C_4H_9)_3N^+-(CH_2)_{10}-N^+(C_4H_9)_3]\cdot(C_{15}H_{31}-SO_4^-)_2$ $[(C_4H_9)_3P^+-(CH_2)_{10}-P^+(C_4H_9)_3]$.

$[(C_4H_9)_3P^+-(CH_2)_{10}-P^+(C_4H_9)_3]$.

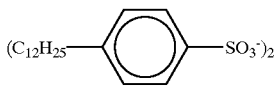

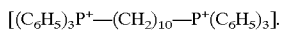

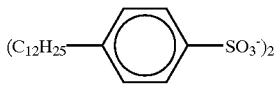

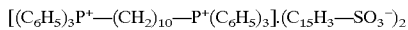

In using these inorganic acidic compounds and organic sulfonic acid compounds, these compounds may be subjected to pretreatment such as ion-exchange treatment to control the acidity according to the purpose.

These acidic compounds may be used singly or in combination.

The amount of the acidic compound to neutralize the residual basic compound is 0.001 mol % to 1 mol %, preferably 0.005 mol % to 0.5 mol % based on 1 mol of the salicylic acid ester derivative.

The amount of the acidic compound for deactivating the catalyst is usually 0.1 to 10 mol-equivalent, preferably 0.5 to 5 mol-equivalent, more preferably 1.0 to 3 mol-equivalent based on the metallic atom or nitrogen atom of the catalyst used in the synthetic reaction.

The shape, type, material and surface-treatment of the apparatus for performing the distillation in the presence of the acidic compounds are arbitrary. Preferably, the distillation is carried out by using a distillation apparatus provided with a distillation column having sufficient theoretical plate number and low pressure loss.

Terminal Blocking Reaction or Polymerization Promoting Reaction

The above-mentioned salicylic acid ester derivative having an impurity content lower than a specific level and the salicylic acid ester derivative produced by the above-mentioned production process can be used in the present invention as a terminal blocking agent or a polymerization promoter in the production of an aromatic polycarbonate. A polycarbonate having excellent color and good color tone can be produced without lowering the terminal blocking reaction rate or the polymerization promoting reaction rate by using the salicylic acid ester derivative disclosed by the present invention.

The reaction scheme of the terminal blocking reaction is as follows.

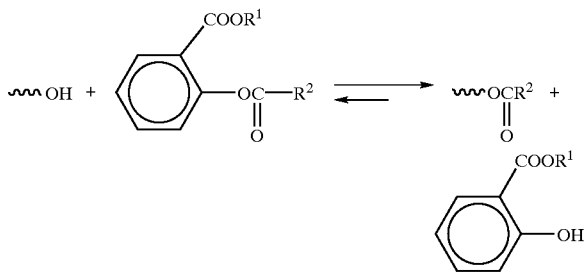

(Scheme 3)

The terminal blocking reaction means the blocking of the hydroxyl group in the terminal group of a polymer with a carbonate bond or an ester bond after the polymerization of a polycarbonate by melt process. Concretely, the terminal blocking reaction can be performed by using the salicylic acid ester derivative composition disclosed in the present invention after sufficiently proceeding the polycondensation reaction of the polycarbonate.

The molecular weight of the polycarbonate to be subjected to the terminal blocking and/or polymerization promoting treatments is usually 0.2 or above, preferably 0.25 to 0.6 and more preferably 0.3 to 0.6 in terms of the intrinsic viscosity $[\eta]$ of the polymer measured in methylene chloride at 20° C.

There is no particular restriction on the method for the addition of the terminal blocking agent, and the agent may be added in solid form or in a form dissolved in various solvents. The prescribed amount of the terminal blocking agent may be added in a lump or in several divided portions provided that the polycondensation reaction is essentially completed at the time of addition.

The amount of the terminal blocking agent in the present invention is 0.1 to 10 times mol, preferably 0.3 to 5 times mol, more preferably 0.5 to 2 times mol based on the terminal hydroxyl group of the polymer at the stage of essentially completed polycondensation reaction.

The pressure condition at the addition of the terminal blocking agent in the present invention is preferably reduced pressure condition to remove phenols generated by the reaction. Concretely, the pressure is 133.32 hPa (100 Torr) or below, preferably 66.66 hPa (50 Torr) or below, more preferably 13.332 hPa (10 Torr) or below. Usually, the reaction is preferably carried out within the pressure range of 1.3332 Pa to 133.32 hPa (0.01 to 100 Torr).

The reaction temperature after the addition of the terminal blocking agent in the present invention is usually 250 to 360° C. and preferably 260 to 340° C. The polymer does not melt at a temperature lower than the above range and the decomposition and discoloration of the polymer may take place at a temperature higher than the above range.

The pressure of the terminal blocking reaction may be normal pressure, however, reduced pressure is preferable for removing phenols generated by the reaction. The pressure is preferably 133.32 hPa (100 Torr) or below, more preferably 13.332 hPa (10 Torr) or below, and especially preferably 1.3332 hPa (1 Torr) or below. The reaction time is usually 1 to 30 minutes, preferably 1 to 20 minutes. Reaction time of 1 to 15 minutes is allowable if desired.

The polymerization promoting reaction means the bonding of hydroxyl terminals of polycarbonate with each other by the use of the above salicylic acid ester derivative to increase the polymerization degree of the polymer.

Salicylic acid ester derivatives usable as the polymerization promoting agent are the compounds of the formula (1) wherein $R^2$ is an aryl group having a carbon number of from 6 to 30, an aryloxy group having a carbon number of from 6 to 30, an aralkyl group having a carbon number of from 6 to 30 or an aralkyloxy group having a carbon number of from 6 to 30, which may have, as a substituent, methoxycarbonyl group, ethoxycarbonyl group, 2-(methoxycarbonyl)phenyloxycarbonyl group, 2-(methoxy-carbonyl)phenyloxycarbonyloxy group, 2-(ethoxycarbonyl)phenyloxy-carbonyl group or 2-(ethoxycarbonyl)phenyloxycarbonyloxy group.

There is no particular restriction on the method for the addition of the polymerization promoting agent, and the agent may be added in solid form or in a form dissolved in various solvents. The prescribed amount of the polymerization promoting agent may be added in a lump or in several divided portions.

There is no particular restriction on the supplying apparatus for supplying the polymerization promoting agent and the reactor for performing the polymerization promoting reaction.

The addition amount of the polymerization promoting agent in the present invention is 0.01 to 1 times mol, preferably 0.03 to 0.7 times mol and more preferably 0.05 to 0.5 times mol based on the terminal hydroxyl group of the prepolymer.

The pressure condition at the addition of the polymerization promoting agent in the present invention is preferably reduced pressure condition to remove phenols generated by the reaction. Concretely, the pressure is 133.32 hPa (100 Torr) or below, preferably 66.66 hPa (50 Torr) or below, and more preferably 13.332 hPa (10 Torr) or below. The reaction is preferably carried out usually within the pressure range of 1.3332 Pa to 133.32 hPa (0.01 to 100 Torr).

The reaction temperature after the addition of the polymerization promoting agent in the present invention is usually 250 to 360° C., preferably 260 to 340 ° C. after the addition of the polymerization promoting agent to the polymer. The polymer does not melt at a temperature lower than the above range and decomposition and discoloration of the polymer take place at a temperature higher than the above range.

The polymerization promoting reaction may be performed under normal pressure condition, however, reduced pressure condition is preferable to remove the phenols generated by the reaction. The pressure is preferably 133.32 hPa (100 Torr) or below, more preferably 13.332 hPa (10 Torr) or below, and especially preferably 1.3332 hPa (1 Torr) or below. The reaction time is usually 1 to 30 minutes, and preferably 1 to 20 minutes. Reaction time of 1 to 15 minutes is allowable if desired.

Recovery of Salicylic Acid Ester

Salicylic acid ester of the above formula (5) is formed by the terminal blocking reaction or the polymerization promoting reaction and, in the present invention, the salicylic acid ester can be recovered and reused as a synthetic raw material for the above terminal blocking agent or the polymerization promoting agent.

The terminal blocking reaction or the polymerization promoting reaction is proceeded at a high temperature (240° C. or above) under reduced pressure (10 Torr or below), and the salicylic acid ester generated in the form of vapor is liquefied and recovered by using a condenser.

Any conventional condensers including water-cooled condensers and air-cooled condensers can be used for the purpose.

Although the recovered salicylic acid ester may be used as it is for the synthesis of the salicylic acid ester derivative according to the above process, it is preferably purified in the present invention before use.

Any conventional purification methods such as washing with a solvent can be used for the purification of the ester, however, the purification by distillation is preferable.

Any conventional distillation apparatuses can be used independent of the type of the apparatus and the material of the distillation still, however, preferable distillation apparatus is those provided with a distillation column and a refluxing column and the distillation column is packed with a filler having low pressure loss. The material of the apparatus is preferably stainless steel such as SUS 316 and SUS 304. The inner surface of the distillation still may be buffed or plated with metal such as chromium.

Aromatic Polycarbonate for Terminal Blocking Reaction

The aromatic polycarbonate to be subjected to the terminal blocking reaction and the polymerization promoting reaction in the present invention means a polycondensation product of an aromatic dihydroxy compound and a carbonic acid diester.

The aromatic dihydroxy compound is a compound expressed by the following formula (13).

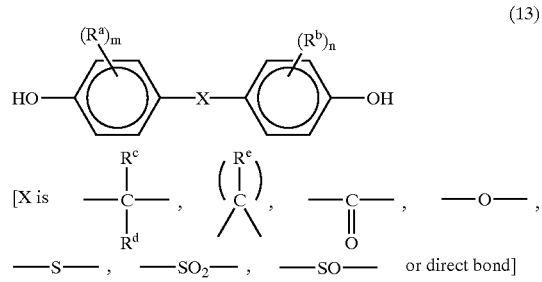

(13)

In the formula (14), $R^a$ and $R^b$ are same or different hydrogen atoms, halogen atoms or hydrocarbon groups having a carbon number of from 1 to 12. The hydrocarbon group is preferably an aliphatic hydrocarbon group having a carbon number of from 1 to 12 or an aromatic hydrocarbon group having a carbon number of from 6 to 12. The halogen atom is chlorine, bromine, iodine or the like.

$R^e$ is an alkylene group having a carbon number of from 3 to 8. Examples of the alkylene group are pentylene group and hexylene group.

In the formula, $R^c$ and $R^d$ are same or different halogen atoms or univalent hydrocarbon groups having a carbon number of from 1 to 12. The hydrocarbon group is, for example, an aliphatic hydrocarbon group having a carbon number of from 1 to 12 or an aromatic hydrocarbon group having a carbon number of from 6 to 12. The halogen atom is chlorine, bromine, iodine or the like.

Concrete examples of the aromatic dihydroxy compound are bis(hydroxyaryl)alkanes such as 1,1-bis(4-hydroxy-t-butylphenyl)propane, 2,2-bis(4-hydroxyphenyl)propane and 2,2-bis(4-hydroxybromophenyl)propane, bis(hydroxyaryl) cycloalkanes such as 1,1-bis(4-hydroxyphenyl) cyclopentane and 1,1-bis(4-hydroxyphenyl)cyclohexane, dihydroxyaryl ethers such as 4,4'-dihydroxydiphenyl ether and 4,4'-dihydroxy-3,3'-dimethylphenyl ether, dihydroxyaryl sulfides such as 4,4'-dihydroxydiphenyl sulfide and 4,4'-dihydroxy-3,3'-dimethylphenyl sulfide, dihydroxyaryl sulfoxides such as 4,4'-dihydroxydiphenyl sulfoxide and 4,4'-dihydroxy-3,3'-dimethylphenyl sulfoxide, and dihydroxyaryl sulfones such as 4,4'-dihydroxydiphenyl sulfone and 4,4'-dihydroxy-3,3'-dimethylphenyl sulfone.

2,2-Bis(4-hydroxyphenyl)propane (bisphenol A) is especially preferable among the above examples. These aromatic dihydroxy compounds may be used singly or in combination.

Concrete examples of the carbonic acid diester compound are diaryl carbonates such as diphenyl carbonate and ditolyl carbonate, dialkyl carbonates such as dimethyl carbonate and diethyl carbonate, and alkyl aryl carbonates such as methyl phenyl carbonate and ethyl phenyl carbonate.

Diphenyl carbonate is especially preferable among the above examples. These carbonic acid diester compounds may be used singly or in combination. The carbonic acid diester compound is preferably used in excess, preferably 1.01 to 1.20 mol based on 1 mol of the aromatic dihydroxy compound.

Any known catalysts can be used as the catalyst for the production of the polymer. Preferable catalysts are alkali metal or alkaline earth metal hydroxide, alcoholate or phenolate, alkali metal or alkaline earth metal salt of organic or inorganic acid, alkali metal or alkaline earth metal salt of oxo acid or ate complex of a group 14 element of the periodic table or a nitrogen-containing basic compound.

The amount of the compound is $10^{-8}$ mol to $10^{-1}$ mol, preferably $10^{-7}$ mol to $10^{-2}$ mol based on 1 mol of the dihydroxy compound used as a raw material for the polycarbonate.

These catalysts may be used singly or in combination.

In the case of using these catalysts in combination, different addition timing and addition method may be used for the catalysts according to the purpose, for example, adding a catalyst compound at the start of polymerization and adding the other catalyst compound during the polymerization process.

The polymerization of polycarbonate (the melt transesterification reaction of a dihydroxy compound with a diaryl carbonate) can be carried out under the same conditions as the conventional known processes.

Concretely, the polycondensation reaction of an aromatic dihydroxy compound and a diaryl carbonate is carried out by reacting an aromatic dihydroxy compound with a diaryl carbonate as the first stage reaction at 80 to 250° C., preferably 100 to 230° C., more preferably 120 to 190° C. for 0.5 to 5 hours, preferably 1 to 4 hours, more preferably 1.5 to 3 hours under reduced pressure, raising the reaction temperature while increasing the vacuum degree of the reaction system to continue the reaction of the aromatic dihydroxy compound with the diaryl carbonate and finally performing the polycondensation reaction of the aromatic dihydroxy compound and the diaryl carbonate at 240 to 320° C. under a reduced pressure of 5 mmHg or below, preferably 1 mmHg or below.

The polycondensation reaction may be performed continuously or in batch. A tank, tubular or column-type reactor may be used as the polymerization apparatus for the above reaction.

A deactivation agent for a catalyst can be added in the present invention to the polymer after the terminal blocking reaction. Any known agents can be used as the catalyst deactivation agent, and the preferable agents are sulfonic acid compounds such as organic sulfonic acid salts, organic sulfonic acid esters, organic sulfonic acid anhydride and organic sulfonic acid betaine.

Especially preferable deactivation agents for catalyst are sulfonic acid salts, particularly organic phosphonium salt and organic ammonium salt of sulfonic acid.

The amount of the catalyst deactivation agent is 0.01 to 500 ppm, preferably 0.01 to 300 ppm based on the polymer.

There is no particular restriction on the reactor for adding the catalyst deactivation agent to the polymer.

In the present invention, the terminal-blocked polycarbonate produced by the above process may be incorporated with conventional heat-stabilizer, ultraviolet absorber, mold-releasing agent, colorant, antistatic agent, lubricant, antifogging agent, natural oil, synthetic oil, wax, organic filler, inorganic filler, etc.

Use

The aromatic polycarbonate produced by the above process has excellent color tone and especially excellent optical properties. Since the chlorine content included by the terminal blocking agent/polymerization promoter can be decreased in the present invention, the metal film formed on the polycarbonate has excellent stability and the polycarbonate is preferably usable for optical materials, especially for optical disk base. The polycarbonate produced according to the present invention causes little peeling of a metallic film, e.g. the evaporated aluminum thin film formed as a recording film on a disk molded from the polycarbonate and, accordingly, the polycarbonate is preferable for the use as an optical disk base.

EXAMPLES

The present invention is described in more detail by the following Examples, which do not restrict the scope of the present invention.

1. Synthesis of Salicylic Acid Ester Derivative

The physical properties cited in the present invention were measured by the following methods.

(i) Elemental analysis: The contents of chlorine and nitrogen were measured by Dorman's microamperometric titration method after burning the sample at 800 to 825° C. The contents of sodium, potassium, iron, chromium and nickel were measured by ICP analysis (Nippon Jarell Ash Co., type ICAP-5751II) on a sample treated at 650° C. and extracted with hydrochloric acid.

(ii) Purity and yield of compound and aromatic hydroxy compound in the raw material: These items were calculated by the formula (the peak area of objective substance)/(total peak area)×100(%)

wherein the peak areas were measured by high-performance liquid chromatography (TOSOH Corp. SC-8020 system, Deversil ODS-7 column manufactured by Nomura Chemical Co., detected by ultraviolet absorption in water/acetonitrile solvent).

The yield was expressed by the molar ratio of the objective product based on the used molar number of the salicylic acid ester (for the Examples 1 to 7) or the carbonic acid diester consisting of an aromatic ester derivative (for the Examples 8 to 11) used as the raw material.

Examples 1 to 7

Reaction was carried out as shown in the following Tables 1 to 4 by using 0.3 mol of the salicylic acid esters and 0.95 times mol (based on the salicylic acid ester) of phosgenes, halogenated formic acid esters or acid halides as raw materials. Coupling reaction was performed by using a sufficient amount of solvent shown in the following Tables 1 to 4 in the presence of a base shown in the following Tables 1 to 4 at 4° C. or below. The coupling was performed under agitation and the amount of the basic compound was 1.05 times mol based on the salicylic acid ester.

The whole quantity of the reaction liquid was successively and thoroughly washed with 0.1N aqueous solution of citric acid, 0.1N aqueous solution of sodium bicarbonate and pure water and dehydrated with anhydrous magnesium sulfate. The solvent was removed from the product and the obtained precipitate was incorporated with acidic compounds shown in the following Tables 1 to 4 (0.01 g each) and purified by distillation. The distillation was performed in high vacuum of 2 torr or below.

Comparative Examples 1 and 2

Reactions similar to the Example 1 were carried out as shown in the Tables 4 and 5 except for the use of 0.3 mol of salicylic acid esters and 1.20 times of a halogenated formic acid ester based on the salicylic acid ester as raw materials. The amount of the base was 1.05 times mol based on the salicylic acid ester.

The whole quantity of the reaction liquid was successively and thoroughly washed by the washing methods shown in the Tables 4 and 5 and dehydrated with anhydrous magnesium sulfate. Tho solvent was removed from the product and the remaining material was recrystallized in a solvent system shown in the Tables 4 and 5.

Examples 8 to 10

Reactions were carried out as shown in the following Tables 6 and 7 by using 1.0 mol of salicylic acid esters and 0.3 times mol of a carbonic acid diester consisting of an aromatic ester derivative based on the salicylic acid ester as raw materials. A three-neck flask having a capacity of 500 ml and provided with a distillation column of 30 cm long was used as the reaction vessel. Transesterification reactions were carried out by using catalysts of the kind and quantity shown in the Tables 6 and 7 under temperature conditions shown in the Tables 6 and 7 while distilling out the aromatic hydroxy compound formed by the reaction from the system. The reaction times were 2 to 4 hours.

After the reaction, the reaction liquid was incorporated with deactivators of the kind and quantity shown in the Tables 6 and 7 and purified by distillation. The distillation was performed in high vacuum of 2 torr or below.

Comparative Examples 3 and 4

Synthetic reactions similar to the Example 8 were carried out as shown in the following Tables 7 and 8 except for the use of 1.0 mol of salicylic acid esters and 0.3 times mol of a carbonic acid diester based on the salicylic acid ester as raw materials.

Example 11

Reaction was carried out as shown in the Table 8 by using 1.0 mol of an aromatic carbonic acid ester and 1.0 mol of a carbonic acid diester consisting of an aromatic ester derivative as raw materials. A flask having a capacity of 500 ml and provided with a stirrer was used as the reaction vessel. Interesterification reaction was carried out by using a catalyst of the kind and quantity shown in the Table 8 under temperature condition shown in the Tables 8.

After the reaction, the reaction liquid was incorporated with a deactivator of the kind and quantity shown in the Table 8 and purified by distillation. The distillation was performed in high vacuum of 2 torr or below.

2. Terminal Blocking Reaction and Polymerization Promoting Reaction of Polycarbonate The physical properties of polymer were measured by the following methods.

(i) Intrinsic viscosity [η]: Intrinsic viscosity was measured in methylene chloride at 20° C. using a Ubbelohde viscometer.

(ii) Quantitative determination of polymer terminal group:
Quantitative determination of terminal group was carried out by dissolving 0.02 gram of a sample in 0.4 ml of a deuterium-substituted chloroform and analyzing by using 1H-NMR (EX-270, product of JEOL Ltd.) at 20° C. The hydroxy terminal concentration (mol %) was calculated by the ratio of each structure to the total terminal number.

Hydroxyl terminal concentration (mol %)=Hydroxyl terminal number (mol)/total terminal number (mol)×100

(iii) Polymer color: Judged by visual inspection.
(iv) Durability of recording film: The evaluation of the obtained polycarbonate as a disk was performed by the durability test on an aluminum thin film (corresponding to a recording film) deposited on a molded disk of the polymer. The obtained polymer was dried (at 120° C. in high vacuum for 12 hours) and injection molded by using a mold for a compact disk (CD). An aluminum thin film (0.1 μmthick) was applied to the molded plate by sputtering. The peeled state of the aluminum thin film was visually observed after holding the film under the condition of 90° C. and 80% relative humidity for 1,000 hours.

Synthesis 1 of Polycarbonate for Terminal Blocking and Polymerization Promotion

A reaction vessel provided with a stirrer, a distiller and an evacuation device was charged with 228 parts of bisphenol A, 220 parts of diphenyl carbonate and catalysts consisting of 1×10 μmol of bisphenol A sodium salt based on 1 mol of bisphenol A and 100×10 μmol of tetramethylammonium hydroxide based on 1 mol of bisphenol A, the atmosphere was substitute with nitrogen and the content was melted at 140° C. After continuing the stirring for 30 minutes, the inner temperature of the reaction vessel was raised to 180° C., the reaction was performed for 30 minutes under a pressure of 100 mmHg and the generated phenol was distilled out. The reaction system was slowly evacuated while raising the temperature to 200° C. and the reaction was continued for 30 minutes under 50 mmHg pressure while distilling out the produced phenol.

The system was further slowly heated and evacuated to 220° C. and 30 mmHg, the reaction was carried out for 30 minutes under the above temperature and pressure condition and the reaction was continued by repeating the heating and evacuation procedures to 240° C. and 10 mmHg, 260° C. and 1 mmHg, and 270° C. and 1 mmHg or below by the procedure same as the above-mentioned procedure.

Finally, the polymerization was carried out for 1 hour under the above temperature and pressure condition, the reaction was stopped when the intrinsic viscosity of the polycarbonate reached about 0.35 and the obtained resin was pelletized.

The intrinsic viscosity [η] of the polymer was 0.344 and the hydroxyl group content (%) was 45%.

Examples 12 to 13

Terminal Blocking Reaction with Salicylic Acid Ester Derivative Synthesized by the Example One hundred (100) parts of the polymer prepared by the above process was melted at 270° C. and incorporated with 2.9 parts of salicylic acid ester derivatives synthesized by the Examples 2 and 8 under reduced pressure condition (50 mmHg). The reaction was continued for 5 minutes at 270° C. under a vacuum of 1 mmHg or below and the intrinsic viscosity [η] and terminal group concentration were measured on each of the obtained polycarbonates. The analytic results of the polycarbonates are shown in the Table 9.

Example 14

Polymerization Promoting Reaction with the Salicylic Acid Ester Derivative Synthesized by the Example One hundred (100) parts of the polymer prepared by the above process was melted at 270° C. and incorporated with 1.5 parts of salicylic acid ester derivative synthesized by the Example 6 under reduced pressure condition (50 mmHg). The reaction was continued for 5 minutes at 270° C. under a vacuum of 1 mmHg or below, and the intrinsic viscosity [η] and terminal group concentration were measured on the obtained polycarbonate. The analytic results of the polycarbonate are shown in the Table 9.

Comparative Examples 5 and 6

Terminal Blocking Reaction with the Salicylic Acid Ester Derivative Synthesized by the Comparative Example One hundred (100) parts of the polymer prepared by the above process was melted at 270° C. and the procedure of the Example 12 was carried out except for the use of 2.9 parts of the salicylic acid ester derivatives synthesized by the Comparative Examples 1 and 2. The analytic results of the obtained polycarbonates are shown in the following Table 10.

3. Recovery of Salicylic Acid Ester

Example 15
Recovery of Salicylic Acid Ester Formed by the Terminal Blocking Reaction Vapor of methyl salicylate formed by the terminal blocking reaction in the Example 12 was recovered by passing the vapor through a water-cooled condenser. Recovered quantity was 1.1 parts by weight based on 2.9 parts by weight of the used salicylic acid ester derivative. The purification of the recovered material by distillation gave 0.84 part by weight of methyl salicylate having a purity of 99%.

Example 16
Synthesis of Salicylic Acid Ester Derivative Using Recovered Salicylic Acid Ester A salicylic acid ester derivative shown in the following Table 11 was synthesized from the methyl salicylate obtained by the Example 15 by a process similar to the Example 2. The results of synthesis are shown in the Table 11.

Example 17
Terminal Blocking Reaction of Polycarbonate with Salicylic Acid Ester Derivative Synthesized by the Example 16

Terminal blocking reaction similar to the Example 12 was performed by using the salicylic acid ester derivative obtained by the Example 16 as the above prepolymer. The obtained results (polymerization degree and the physical properties of the polymer) are shown in the following Table 12.

TABLE 1

|  | Example 1 | Example 2 |
|---|---|---|
| Salicylic acid ester derivative | [structure with COOCH₃ group, bisphenol A linkage] | [structure with COOCH₃ group, phenyl linkage] |
| Raw material | methyl salicylate / p-cumylphenyl chloroformate | methyl salicylate / phenyl chloroformate |
| Impurities in raw material | | |
| Cl (ppm) | — / — | — / — |
| N (ppm) | — / — | — / — |
| Metal (ppm) | — / — | 6 / 7 |
| Water (%) | — / — | — / — |
| Aromatic hydroxy compound (%) | — / — | — / — |
| Reaction conditions | | |
| Basic compd | triethylamine | pyridine |
| Solvent | dichloromethane | dichloromethane |
| Washing method | washing (1) (*1) | washing (1) (*1) |
| Distillation | | |
| Inorganic acid | phosphoric acid | diphosphorus pentoxide |
| Sulfonic acid | — | — |
| Recrystallization | — | — |
| Product | | |
| Purity (%) | 97 | 96 |
| Yield (%) | 88 | 90 |
| Impurities | | |
| Cl (ppm) | 8 | 9 |
| N (ppm) | — | — |
| Metal (ppm) | — | 5 |

(*1) Washing (1): Successively washed with 0.1 N aqueous solution of citric acid, 0.1 N aqueous solution of sodium bicarbonate and pure water

TABLE 2

| | Example 3 | | Example 4 | |
|---|---|---|---|---|
| Salicylic acid ester derivative | 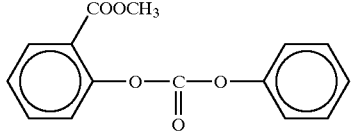 | | 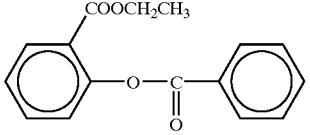 | |
| Raw material | methyl salicylate | phenyl chloroformate | ethyl salicylate | benzoyl chloride |
| Impurities in raw material | | | | |
| Cl (ppm) | — | — | — | — |
| N (ppm) | — | — | 2 | <1 |
| Metal (ppm) | 2 | <1 | 5 | 3 |
| Water (%) | 3 | 2 | 1 | <1 |
| Aromatic hydroxy compound (%) | — | — | 2 | <1 |
| Reaction conditions | | | | |
| Basic compd | trimethylamine | | sodium hydroxide | |
| Solvent | dichloromethane | | dichloromethane | |
| Washing method | washing (1) | | washing (1) | |
| Distillation | | | | |
| Inorganic acid | sulfuric acid | | — | |
| Sulfonic acid | — | | p-toluenesulfonic acid | |
| Recrystallization | — | | — | |
| Product | | | | |
| Purity (%) | 95 | | 96 | |
| Yield (%) | 89 | | 86 | |
| Impurities | | | | |
| Cl (ppm) | 10 | | 7 | |
| N (ppm) | 7 | | 5 | |
| Metal (ppm) | 3 | | 2 | |

TABLE 3

| | Example 5 | | Example 6 | |
|---|---|---|---|---|
| Salicylic acid ester derivative | 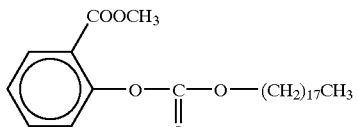 | | 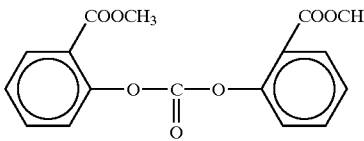 | |
| Raw material | methyl salicylate | stearyl chloroformate | methyl salicylate | phosgene dimer |
| Impurities in raw material | | | | |
| Cl (ppm) | 8 | — | 5 | — |
| N (ppm) | 3 | <1 | 1 | <1 |
| Metal (ppm) | 2 | 2 | <1 | 1 |
| Water (%) | 3 | 1 | 1 | 1 |
| Aromatic hydroxy compound (%) | 1 | <1 | <1 | <1 |
| Reaction conditions | | | | |
| Basic compd | triethylamine | | ammonia | |
| Solvent | dichloromethane | | dichloromethane-water | |
| Washing method | washing (1) | | washing (1) | |
| Distillation | | | | |
| Inorganic acid | — | | — | |
| Sulfonic acid | — | | — | |
| Recrystallization | xylene-heptane | | xylene-heptane | |
| Product | | | | |
| Purity (%) | 91 | | 96 | |

TABLE 3-continued

|  | Example 5 | Example 6 |
| --- | --- | --- |
| Yield (%) | 81 | 90 |
| Impurities |  |  |
| Cl (ppm) | 11 | 6 |
| N (ppm) | — | 3 |
| Metal (ppm) | — | 2 |

TABLE 4

|  | Example 7 |  |  | Comparative Example 1 |  |
| --- | --- | --- | --- | --- | --- |
| Salicylic acid ester derivative | 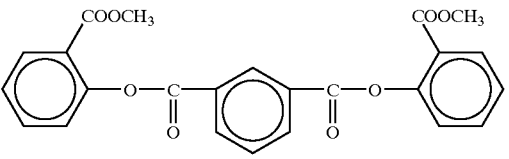 | | | 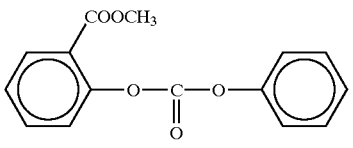 | |
| Raw material | methyl salicylate | isophthaloyl dichloride | | methyl salicylate | phenyl chloroformate |
| Impurities in raw material | | | | | |
| Cl (ppm) | 8 | — | | — | — |
| N (ppm) | 3 | — | | — | — |
| Metal (ppm) | 2 | — | | — | — |
| Water (%) | 3 | 2 | | — | — |
| Aromatic hydroxy compound (%) | 1 | — | | — | — |
| Reaction conditions | | | | | |
| Basic compd | triethylamine | | | triethylamine | |
| Solvent | xylene | | | dichloromethane | |
| Washing method | washing (1) | | | washing (2) *2 | |
| Distillation | | | | | |
| Inorganic acid | — | | | phosphoric acid | |
| Sulfonic acid | — | | | | |
| Recrystallization | xylene-heptane | | | | |
| Product | | | | | |
| Purity (%) | 92 | | | 94 | |
| Yield (%) | 84 | | | — | |
| Impurities | | | | | |
| Cl (ppm) | 8 | | | 190 | |
| N (ppm) | — | | | — | |
| Metal (ppm) | — | | | — | |

*2 Washing (2): Reaction liquid was successively washed with 1% HCl and pure water.

TABLE 5

|  | Comparative Example 2 | |
| --- | --- | --- |
| Salicylic acid ester derivative | 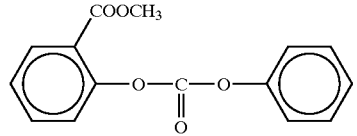 | |
| Raw material | methyl salicylate | phenyl chloroformate |
| Impurities in raw material | | |
| Cl (ppm) | — | — |
| N (ppm) | — | — |
| Metal (ppm) | 220 | — |
| Water (%) | — | — |
| Aromatic hydroxy compound (%) | — | — |
| Reaction conditions | | |
| Basic compd | triethylamine | |
| Solvent | dichloromethane | |
| Washing method | washing (3) *3 | |
| Distillation | | |
| Inorganic acid | — | |
| Sulfonic acid | — | |
| Recrystallization | xylene-heptane | |
| Product | | |
| Purity (%) | 97 | |

TABLE 5-continued

| | Comparative Example 2 |
|---|---|
| Yield (%) | — |
| Impurities | |
| Cl (ppm) | 360 |
| N (ppm) | — |
| Metal (ppm) | 43 |

*3 Washing (3): Reaction liquid was washed with pure water.

TABLE 6

| | Example 8 | | Example 9 | |
|---|---|---|---|---|
| Salicylic acid ester derivative | methyl salicylate-O-C(=O)-O-phenyl (with COOCH₃) | | ethyl salicylate-O-C(=O)-O-phenyl (with COOCH$_2$CH$_3$) | |
| Raw material | methyl salicylate | diphenyl carbonate | ethyl salicylate | diphenyl carbonate |
| Impurities in raw material | | | | |
| Cl (ppm) | 2 | — | 3 | 3 |
| N (ppm) | — | — | <1 | — |
| Metal (ppm) | — | — | 1 | 2 |
| Water (%) | — | — | — | — |
| Aromatic hydroxy compound (%) | — | — | — | — |
| Reaction conditions | | | | |
| Catalyst | La$_2$O$_3$ | | tetramethylammonium hydroxide | |
| Amount (g) | 1.0 | | 0.1 | |
| Temp. (° C.) | 200 | | 200 | |
| Distillation | | | | |
| Inorganic acid | phosphoric acid | | talc | |
| Sulfonic acid | — | | — | |
| Recrystallization | — | | — | |
| Product | | | | |
| Purity (%) | 96 | | 94 | |
| Yield (%) | 40 | | 36 | |
| Impurities | | | | |
| Cl (ppm) | 1 | | 2 | |
| N (ppm) | — | | 1 | |
| Metal (ppm) | — | | 1 | |

TABLE 7

| | Example 10 | | Comparative Example 3 | |
|---|---|---|---|---|
| Salicylic acid ester derivative | methyl salicylate-O-C(=O)-phenyl-C(=O)-O-CH₃ (with COOCH₃) | | methyl salicylate-O-C(=O)-O-phenyl (with COOCH₃) | |
| Raw material | methyl salicylate | methyl phenyl terephthalate | methyl salicylate | diphenyl carbonate |
| Impurities in raw material | | | | |

TABLE 7-continued

|  | Example 10 | | Comparative Example 3 | |
| --- | --- | --- | --- | --- |
| Cl (ppm) | 2 | 3 | 320 | — |
| N (ppm) | 3 | <1 | — | — |
| Metal (ppm) | 3 | 4 | — | — |
| Water (%) | 2 | 1 | — | — |
| Aromatic hydroxy compound (%) | <1 | <1 | — | — |
| Reaction conditions | | | | |
| Catalyst | zinc stearate | | La$_2$O$_3$ | |
| Amount (g) | 0.2 | | 1.0 | |
| Temp. (° C.) | 200 | | 200 | |
| Distillation | | | | |
| Inorganic acid | — | | phosphoric acid | |
| Sulfonic acid | dodecylbenzenesulfonic acid tetrabutylphosphonium | | — | |
| Recrystallization | | | | |
| Product | | | | |
| Purity (%) | 93 | | — | |
| Yield (%) | 30 | | <1 | |
| Impurities | | | | |
| Cl (ppm) | 1 | | — | |
| N (ppm) | <1 | | — | |
| Metal (ppm) | 3 | | — | |

TABLE 8

|  | Comparative Example 4 | | Example 11 | |
| --- | --- | --- | --- | --- |
| Salicylic acid ester derivative | (structure) | | (structure) | |
| Raw material | (structure) | diphenyl carbonate | (structure) | diphenyl carbonate |
| Impurities in raw material | | | | |
| Cl (ppm) | — | 400 | 3 | 2 |
| N (ppm) | — | — | — | — |
| Metal (ppm) | — | — | — | — |
| Water (%) | — | — | — | — |
| Aromatic hydroxy compound % | — | — | — | — |
| Reaction conditions | | | | |
| Catalyst | La$_2$O$_3$ | | sodium hydroxide | |
| Amount (g) | 1.0 | | 0.01 | |
| Temp. (° C.) | 200 | | 200 | |
| Distillation | | | | |
| Inorganic acid | phosphoric acid | | phosphoric acid | |
| Sulfonic acid | — | | — | |
| Recrystallization | — | | — | |
| Product | | | | |
| Purity (%) | — | | 93 | |
| Yield (%) | <1 | | — | |

TABLE 8-continued

|  | Comparative Example 4 | Example 11 |
|---|---|---|
| Impurities |  |  |
| Cl (ppm) | — | 2 |
| N (ppm) | — | — |
| Metal (ppm) | — | — |

TABLE 9

|  | Example 12 | Example 13 | Example 14 |
|---|---|---|---|
| Salicylic acid ester derivative Structure | (structure with COOCH$_3$, carbonate linkage to phenyl) | (structure with COOCH$_3$, carbonate linkage to phenyl) | (structure with COOCH$_3$ on both phenyl rings, carbonate linkage) |
| Property of polymer [η] | 0.354 | 0.351 | 0.571 |
| OH terminal (mol %) | 4 | 3 | 8 |
| Color | good | good | good |
| Peeling of film | little | little | — |

TABLE 10

|  | Comparative Example 5 | Comparative Example 6 |
|---|---|---|
| Salicylic acid ester derivative Structure | (structure with COOCH$_3$, carbonate linkage to phenyl) | (structure with COOCH$_3$, carbonate linkage to phenyl) |
| Property of polymer [η] | 0.343 | 0.335 |
| OH terminal (mol %) | 42 | 43 |
| Color | a little colored | remarkably colored |
| Peeling of film | much | much |

TABLE 11

|  | Example 16 | |
|---|---|---|
| Salicylic acid ester derivation | (structure with COOCH$_3$, carbonate linkage to phenyl) | |
| Raw material | methyl salicylate | phenyl chloroformate |
| Impurities in raw material |  |  |
| Cl (ppm) | — | — |
| N (ppm) | — | — |
| Metal (ppm) | — | — |
| Water (%) | — | — |
| Aromatic hydroxy compound (%) | — | — |
| Reaction conditions |  |  |
| Basic compd | triethylamine | |
| Solvent | dichloromethane | |
| Washing method | washing (1) *1 | |
| Distillation |  |  |
| Inorganic acid | phosphoric acid | |
| Sulfonic acid | — | |

TABLE 11-continued

| | Example 16 |
|---|---|
| Recrystallization Product | — |
| Purity (%) | 95 |
| Yield (%) | 88 |
| Impurities | |
| Cl (ppm) | 5 |
| N (ppm) | — |
| Metal (ppm) | — |

*1 Washing (1): Successively washed with 0.1 N aqueous solution of citric acid, 0.1 N aqueous solution of sodium bicarbonate and pure water.

TABLE 12

| | Example 17 |
|---|---|
| Salicylic acid ester derivative Structure | 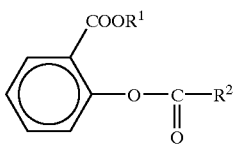 |
| Property of polymer [η] | 0.349 |
| OH terminal (mol %) | 5 |
| Color | good |
| Peeling of film | little |

What is claimed is:

1. A salicylic acid ester derivative having a chlorine content of 10 ppm or below and expressed by the following formula (1)

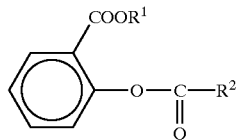

in the formula, $R^1$ is methyl group or ethyl group, $R^2$ is an alkyl group having a carbon number of from 1 to 30, an alkoxy group having a carbon number of from 1 to 30, an aryl group having a carbon number of from 6 to 30, an aryloxy group having a carbon number of from 6 to 30, an aralkyl group having a carbon number of from 6 to 30 or an aralkyloxy group having a carbon number of from 6 to 30; the group $R^2$ may have, as a substituent, methoxycarbonyl group, ethoxycarbonyl group, 2-(methoxycarbonyl)phenyloxycarbonyl group, 2-(methoxycarbonyl)phenyloxycarbonyloxy group, 2-(ethoxycarbonyl)phenyloxycarbonyl group, 2-(ethoxycarbonyl)phenyloxycarbonyloxy group or an aryloxycarbonyl group or aralkyloxycarbonyl group having a carbon number of from 6 to 10.

2. A salicylic acid ester derivative described in the claim 1 provided that the total nitrogen content is 100 ppm or below.

3. A salicylic acid ester derivative described in claim 1 provided that the sum of the netallic elements contained in the derivative is 30 ppm or below.

4. A salicylic acid ester derivative described in claim 2 provided that the sum of the metallic elements contained in the derivative is 30 ppm or below.

5. A process for producing a salicylic acid ester derivative expressed by the following formula (1)

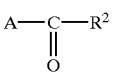

(in the formula, $R^1$ is methyl group or ethyl group, $R^2$ is an alkyl group having a carbon number of from 1 to 30, an alkoxy group having a carbon number of from 1 to 30, an aryl group having a carbon number of from 6 to 30, an aryloxy group having a carbon number of from 6 to 30, an aralkyl group having a carbon number of from 6 to 30; the group $R^2$ may have, as a substituent, methoxycarbonyl group, ethoxycarbonyl group, 2-(methoxycarbonyl)phenyloxycarbonyl group, 2-(methoxycarbonyl)phenyloxycarbonyloxy group, 2-(ethoxycarbonyl)phenyloxycarbonyl group, 2-(ethoxycarbonyl)phenyloxycarbonyloxy group or an aryloxycarbonyl group or aralkyloxycarbonyl group having a carbon number of from 6 to 10) by reacting phosgenes or an acid halide compound or halogenated formic acid ester expressed by the following formulas (2), (3) or (4)

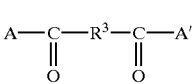

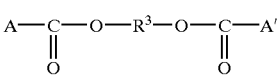

(in the formulas, A and A' are each a halogen, $R^2$ is same as the definition in the formula (1), and $R^3$ is a bivalent alkylene group, arylene group or aralkylene group having a carbon number of from 1 to 30) with a salicylic acid ester expressed by the following formula (5)

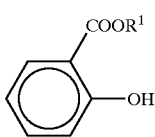

(in the formula, $R^1$ is methyl group or ethyl group) in the presence of a basic compound.

6. A process for the production of a salicylic acid ester derivative described in claim 5 provided that the total amount of metallic elements contained in each of at least one halide selected from the phosgenes and an acid halide compound or halogenated formic acid ester expressed by the above formulas (2) to (4) and the salicylic acid ester expressed by the above formula (5) is 100 ppm or below.

7. A salicylic acid ester derivative described in claim 1 characterized in that said salicylic acid ester derivative is described by the following formula (1)-2

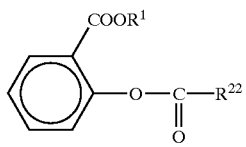

(in the formula (1)-2, $R^1$ is methyl group or ethyl group, $R^{22}$ is an aryl group having a carbon number of from 6 to 30, an aryloxy group having a carbon number of from 6 to 30, an aralkyl group having a carbon number of from 6 to 30, or an aralkyloxy group having a carbon number of from 6 to 30; the group $R^{22}$ may have, as a substituent methoxycarbonyl group, ethoxycarbonyl group, 2-(methoxycarbonyl) phenyloxycarbonyl group, 2-(methoxycarbonyl) phenyloxycarbonyloxy group, 2-(ethoxycarbonyl) phenyloxycarbonyl group, 2-(ethoxycarbonyl) phenyloxycarbonyloxy group or an aryloxycarbonyl group or aralkyloxycarbonyl group having a carbon number of from 6 to 10).

8. A salicylic acid ester derivative described in claim 2 characterized in that said salicylic acid ester derivative is described by the following formula (1)-2

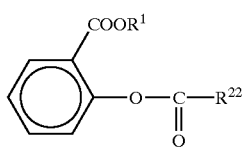

(in the formula (1)-2, $R^1$ is methyl group or ethyl group, $R^{22}$ is an aryl group having a carbon number of from 6 to 30, an aryloxy group having a carbon number of from 6 to 30, an aralkyl group having a carbon number of from 6 to 30, or an aralkyloxy group having a carbon number of from 6 to 30; the group $R^{22}$ may have, as a substituent, methoxycarbonyl group, ethoxycarbonyl group, 2-(methoxycarbonyl) phenyloxycarbonyl group, 2-(methoxycarbonyl) phenyloxycarbonyloxy group, 2-(ethoxycarbonyl) phenyloxycarbonyl group, 2-(ethoxycarbonyl) phenyloxycarbonyloxy group or an aryloxycarbonyl group or aralkyloxycarbonyl group having a carbon number of from 6 to 10).

9. A salicylic acid ester derivative described in claim 3 characterized in that said salicylic acid ester derivative is described by the following formula (1)-2

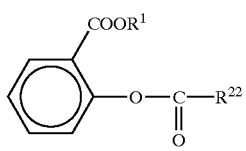

(in the formula (1)-2, $R^1$ is methyl group or ethyl group, $R^{22}$ is an aryl group having a carbon number of from 6 to 30, an aryloxy group having a carbon number of from 6 to 30, an aralkyl group having a carbon number of from 6 to 30, or an aralkyloxy group having a carbon number of from 6 to 30; the group $R^{22}$ may have, as a substituent, methoxycarbonyl group, ethoxycarbonyl group, 2-(methoxycarbonyl) phenyloxycarbonyl group, 2-(methoxycarbonyl) phenyloxycarbonyloxy group, 2-(ethoxycarbonyl) phenyloxycarbonyl group, 2-(ethoxycarbonyl) phenyloxycarbonyloxy group or an aryloxycarbonyl group or aralkyloxycarbonyl group having a carbon number of from 6 to 10).

10. A salicylic acid ester derivative described in claim 4 characterized in that said salicylic acid ester derivative is described by the following formula (1)-2

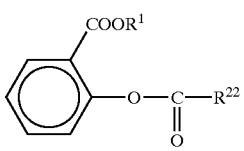

(in the formula (1)-2, $R^1$ is methyl group or ethyl group, $R^{22}$ is an aryl group having a carbon number of from 6 to 30, an aryloxy group having a carbon number of from 6 to 30, an aralkyl group having a carbon number of from 6 to 30, or an aralkyloxy group having a carbon number of from 6 to 30; the group $R^{22}$ may have, as a substituent, methoxycarbonyl group, ethoxycarbonyl group, 2-(methoxycarbonyl) phenyloxycarbonyl group, 2-(methoxycarbonyl) phenyloxycarbonyloxy group, 2-(ethoxycarbonyl) phenyloxycarbonyl group, 2-(ethoxycarbonyl) phenyloxycarbonyloxy group or an aryloxycarbonyl group or aralkyloxycarbonyl group having a carbon number of from 6 to 10).

11. A process for the production of a salicylic acid ester derivative expressed by the following formula (1)-2

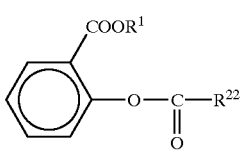

in the formula (1)-2, $R^1$ is methyl group or ethyl group, $R^{22}$ is an aryl group having a carbon number of from 6 to 30, an aryloxy group having a carbon number of from 6 to 30, an aralkyl group having a carbon number of from 6 to 30, or an aralkyloxy group having a carbon number of from 6 to 30; the group $R^{22}$ may have, as a substituent, methoxycarbonyl group, ethoxycarbonyl group, 2-(methoxycarbonyl) phenyloxycarbonyl group, 2-(methoxycarbonyl) phenyloxycarbonyloxy group, 2-(ethoxycarbonyl) phenyloxycarbonyl group, 2-(ethoxycarbonyl) phenyloxycarbonyloxy group or an aryloxycarbonyl group or aralkyloxycarbonyl group having a carbon number of from 6 to 10, comprising reacting an aromatic ester derivative expressed by the following formula (6)

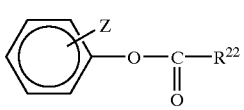

in the formula (6), Z groups are same or different groups selected from hydrogen atom and an alkyl group having a carbon number of from 1 to 4, and $R^{22}$ is same as the group defined in the above formula (1)-2, and a salicylic acid ester expressed by the following formula (5)

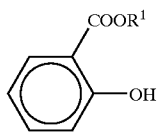

(5)

in the presence of a catalyst.

12. A process for the production of a salicylic acid ester derivative expressed by the above formula (1)-2

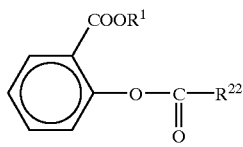

(1)-2 in the formula (1)-2, $R^1$ is methyl group or ethyl group, $R^{22}$ is an aryl group having a carbon number of from 6 to 30, an aryloxy group having a carbon number of from 6 to 30, an aralkyl group having a carbon number of from 6 to 30, or an aralkyloxy group having a carbon number of from 6 to 30; the group $R^{22}$ may have, as a substituent, methoxycarbonyl group, ethoxycarbonyl group, 2-(methoxycarbonyl) phenyloxycarbonyl group, 2-(methoxycarbonyl) phenyloxycarbonyloxy group, 2-(ethoxycarbonyl) phenyloxycarbonyl group, 2-(ethoxycarbonyl) phenyloxycarbonyloxy group or an aryloxycarbonyl group or aralkyloxycarbonyl group having a carbon number of from 6 to 10, comprising reacting an aromatic ester derivative expressed by the following formula (6)-2

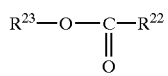

(6)-2 in the formula, Z groups are same or different groups selected from hydrogen atom and an alkyl group having a carbon number of from 1 to 4, $R^{22}$ is same as the group defined in the above formula (1)-2, and $R^{23}$ is an aryl group having a carbon number of from 1 to 30 or an aralkyl group having a carbon number of from 1 to 30, and an aromatic carbonic acid ester expressed by the following formula (7)

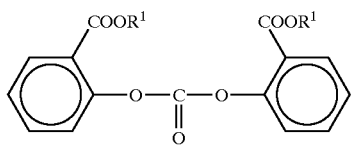

(7)

in the formula, $R^1$ is methyl group or ethyl group, in the presence of a catalyst.

13. A process for the production of a salicylic acid ester derivative described in claim 11 provided that the chlorine content of each of the salicylic acid ester expressed by the above formula (5) and the aromatic ester derivative expressed by the above formula (6) is 100 ppm or below.

14. A process for the production of a salicylic acid ester derivative described in claim 12 provided that the chlorine content of each of the salicylic acid ester expressed by the above formula (5), the aromatic ester derivative expressed by the above formula (6) or (6)-2 and the aromatic carbonic acid ester expressed by the above formula (7) is 100 ppm or below.

15. A process for the production of a salicylic acid ester derivative described in claim 11 provided that the total amount of metals contained in each of the salicylic acid ester expressed by the above formula (5) and the aromatic ester derivative expressed by the above formula (6) is 50 ppm or below.

16. A process for the production of a salicylic acid ester derivative described in claim 12 provided that the total amount of metals contained in each of the salicylic acid ester expressed by the above formula (5), the aromatic ester derivative expressed by the above formula (6) or (6)-2 and the aromatic carbonic acid ester expressed by the above formula (7) is 50 ppm or below.

17. A process for the production of a salicylic acid ester derivative described in claim 5 provided that the water content of each of the halogens, the halide expressed by the above formulas (2) to (4) and the salicylic acid ester expressed by the above formula (5) is 5% by weight or below.

18. A process for the production of a salicylic acid ester derivative described in claim 11 provided that the water content of each of the halogens, the halide expressed by the above formulas (2) to (4), the salicylic acid ester expressed by the above formula (5), and the aromatic ester derivative expressed by the above formula (6) is 5% by weight or below.

19. A process for the production of a salicylic acid ester derivative described in claim 12 provided that the water content of each of the halogens, the halide expressed by the above formulas (2) to (4), the salicylic acid ester expressed by the above formula (5) and the aromatic ester derivative expressed by the above formula (6) is 5% by weight or below.

20. A process for the production of a salicylic acid ester derivative described in claim 5 provided that the content of aromatic monohydroxy compounds in each of the halogens, the halide expressed by the above formulas (2) to (4), and the salicylic acid ester expressed by the above formula (5) is 3% by weight or below.

21. A process for the production of a salicylic acid ester derivative described in claim 11 provided that the content of aromatic monohydroxy compounds in each of the halogens, the halide expressed by the above formulas (2) to (4), the salicylic acid ester expressed by the above formula (5), and the aromatic ester derivative expressed by the above formula (6) is 3% by weight or below.

22. A process for the production of a salicylic acid ester derivative described in claim 12 provided that the content of aromatic monohydroxy compounds in each of the halogens, the halide expressed by the above formulas (2) to (4), the salicylic acid ester expressed by the above formula (5), the aromatic ester derivative expressed by the above formula (6) or (6)-2 and the aromatic ester expressed by the above formula (7) is 3% by weight or below.

23. A process for the production of a salicylic acid ester derivative described in claim 11 provided that the catalyst is a compound of an alkali metal, an alkaline earth metal or an element of the group 3 or group 12 of the periodic table.

24. A process for the production of a salicylic acid ester derivative described in claim 12 provided that the catalyst is a compound of an alkali metal, an alkaline earth metal or an element of the group 3 or group 12 of the periodic table.

25. A process for the production of a salicylic acid ester derivative described in claim 13 provided that the catalyst is a compound of an alkali metal, an alkaline earth metal or an element of the group 3 or group 12 of the periodic table.

26. A process for the production of a salicylic acid ester derivative described in claim 14 provided that the catalyst is a compound of an alkali metal, an alkaline earth metal or an element of the group 3 or group 12 of the periodic table.

27. A process for the production of a salicylic acid ester derivative described in claim 23 provided that the catalyst is at least one kind of material selected from lanthanum oxide, calcium oxide, lanthanum alkoxide and zinc carboxylate.

28. A process for the production of a salicylic acid ester derivative described in claim 24 provided that the catalyst is at least one kind of material selected from lanthanum oxide, calcium oxide, lanthanum alkoxide and zinc carboxylate.

29. A process for the production of a salicylic acid ester derivative described in claim 25 provided that the catalyst is at least one kind of material selected from lanthanum oxide, calcium oxide, lanthanum alkoxide and zinc carboxylate.

30. A process for the production of a salicylic acid ester derivative described in claim 26 provided that the catalyst is at least one kind of material selected from lanthanum oxide, calcium oxide, lanthanum alkoxide and zinc carboxylate.

31. A process described in claim 27 provided that the catalyst is a lanthanum oxide and the weight reduction of the oxide heated at 500° C. for 1 hour is 3% or less.

32. A process described in claim 28 provided that the catalyst is a lanthanum oxide and the weight reduction of the oxide heated at 500° C. for 1 hour is 3% or less.

33. A process described in claim 29 provided that the catalyst is a lanthanum oxide and the weight reduction of the oxide heated at 500° C. for 1 hour is 3% or less.

34. A process described in claim 30 provided that the catalyst is a lanthanum oxide and the weight reduction of the oxide heated at 500° C. for 1 hour is 3% or less.

35. A process for the production of a salicylic acid ester derivative described in claim 11 provided that the catalyst is at least one kind of material selected from nitrogen-containing basic compounds and phosphorus-containing basic compounds.

36. A process for the production of a salicylic acid ester derivative described in claim 12 provided that the catalyst is at least one kind of material selected from nitrogen-containing basic compounds and phosphorus-containing basic compounds.

37. A process for the production of a salicylic acid ester derivative described in claim 13 provided that the catalyst is at least one kind of material selected from nitrogen-containing basic compounds and phosphorus-containing basic compounds.

38. A process for the production of a salicylic acid ester derivative described in claim 14 provided that the catalyst is at least one kind of material selected from nitrogen-containing basic compounds and phosphorus-containing basic compounds.

39. A process for the production of a salicylic acid ester derivative described in claim 5 provided that the catalyst described in claim 11 or 12 and/or the basic compound described in the claim 5 and remaining after the reaction are deactivated and/or neutralized by the addition of a least one kind of compound selected from an acidic compound comprising an inorganic acidic compound or an organic sulfonic acid compound, a salt of said acidic compound and a derivative of said acidic compound.

40. A process for the production of a salicylic acid ester derivative described in claim 11 provided that the catalyst described in the claim 11 or 12 and/or the basic compound described in the claim 5 and remaining after the reaction are deactivated and/or neutralized by the addition of a least one kind of compound selected from an acidic compound comprising an inorganic acidic compound or an organic sulfonic acid compound, a salt of said acidic compound and a derivative of said acidic compound.

41. A process for the production of a salicylic acid ester derivative described in claim 12 provided that the catalyst described in the claim 11 or 12 and/or the basic compound described in the claim 5 and remaining after the reaction are deactivated and/or neutralized by the addition of a least one kind of compound selected from an acidic compound comprising an inorganic acidic compound or an organic sulfonic acid compound, a salt of said acidic compound and a derivative of said acidic compound.

42. A process for the production of a salicylic acid ester derivative described in claim 39 provided that said inorganic acidic compound is phosphoric acid and/or its condensation product.

43. A process for the production of a salicylic acid ester derivative described in claim 40 provided that said inorganic acidic compound is phosphoric acid and/or its condensation product.

44. A process for the production of a salicylic acid ester derivative described in claim 41 provided that said inorganic acidic compound is phosphoric acid and/or its condensation product.

45. A process for the production of a salicylic acid ester derivative described in claim 40 provided that said inorganic acidic compound is a solid acid.

46. A process for the production of a salicylic acid ester derivative described in claim 41 provided that said inorganic acidic compound is a solid acid.

47. A process described in claim 40 wherein said organic sulfonic acid compound is expressed by the following general formula (8)

$$A^1-(Y^1-SO_3X^1)_m \quad (8)$$

(wherein $A^1$ is an m-valent hydrocarbon group having a carbon number of from 1 to 30, which may have a substituent or not, $Y^1$ is single bond or oxygen atom, $X^1$ is hydrogen atom, a secondary or tertiary univalent hydrocarbon group having a carbon number of from 2 to 30, or one equivalent of metallic cation, ammonium cation or phosphonium cation, and m is an integer of 1 to 4);

the following general formula (9)

$$^+X^2-A^2-Y^1-SO_3^- \quad (9)$$

(wherein $A^2$ is a bivalent hydrocarbon group having a carbon number of from 1 to 30, $^+X^2$ is a secondary to quaternary ammonium cation or a secondary to quaternary phosphonium cation, and the definition of $Y^1$ is same as the definition in the above formula (8));

or the following general formula (10)

$$A^3-(^+X^3)_n\cdot(R-Y^1-SO_3^-)_n \quad (10)$$

(wherein $A^3$ is an n-valent hydrocarbon group having a carbon number of from 1 to 30, $^+X^3$ is a secondary to quaternary ammonium cation or a secondary to quaternary phosphonium cation, R is a univalent hydrocarbon group having a carbon number of from 1 to 30, n is an integer of 2 to 4, and the definition of $Y^1$ is same as the definition in the above formula (8)).

48. A process described in claim 41 wherein said organic sulfonic acid compound is expressed by the following general formula (8)

$$A^1-(Y^1-SO_3X^1)_m \quad (8)$$

(wherein $A^1$ is an m-valent hydrocarbon group having a carbon number of from 1 to 30, which it may have a substituent or not, $Y^1$ is single bond or oxygen atom, $X^1$ is hydrogen atom, a secondary or tertiary univalent hydrocarbon group having a carbon number of from 2 to 30, or one equivalent of metallic cation, ammonium cation or phosphonium cation, and m is an integer of 1 to 4), the following general formula (9)

$$^+X^2\text{—}A^2\text{—}Y^1\text{—}SO_3^- \qquad (9)$$

(wherein $A^2$ is a bivalent hydrocarbon group having a carbon number of from 1 to 30, $^+X^2$ is a secondary to quaternary ammonium cation or a secondary to quaternary phosphonium cation, and the definition of $Y^1$ is same as the definition in the above formula (8));
or the following general formula (10)

$$A^3\text{—}(^+X^3)_n\text{·}(R\text{—}Y^1\text{—}SO_3^-)_n \qquad (10)$$

(wherein $A^3$ is an n-valent hydrocarbon group having a carbon number of from 1 to 30, $^+X^3$ is a secondary to quaternary ammonium cation or a secondary to quaternary phosphonium cation, R is a univalent hydrocarbon group having a carbon number of from 1 to 30, n is an integer of 2 to 4, and the definition of $Y^1$ is same as the definition in the above formula (8)).

49. A process described in claim 40 provided that the amount of said acidic compound is 0.001 to 1% by weight based on the salicylic acid ester derivative expressed by the above formula (1)-2.

50. A process described in claim 41 provided that the amount of said acidic compound is 0.001 to 1% by weight based on the salicylic acid ester derivative expressed by the above formula (1)-2.

51. A process for the production of salicylic acid ester derivative described in any one of claim 5 or 13 to 41 characterized in that the salicylic acid ester of the above formula (5) formed by the terminal blocking reaction using a salicylic acid ester derivative expressed by the above formula (11) as a terminal blocking agent or by the polymerization promoting reaction using a salicylic acid ester derivative expressed by the above formula (1) wherein $R^2$ is an aryl group having a carbon number of from 6 to 30, an aryloxy group having a carbon number of from 6 to 30, an aralkyl group having a carbon number of from 6 to 30 or an aralkyloxy group having a carbon number of from 6 to 30 and may have, as a substituent, methoxycarbonyl group, ethoxycarbonyl group, 2-(methoxycarbonyl)phenyloxycarbonyl group, 2-(methoxycarbonyl)phenyloxycarbonyloxy group, 2-(ethoxycarbonyl)phenyloxycarbonyl group, or 2-(ethoxycarbonyl)phenyloxycarbonyloxy group as a polymerization promoting agent is recovered and the recovered salicylic ester is used in the production of an aromatic polycarbonate by a melt process.

52. A process for the production of salicylic acid ester derivative described in claim 11 characterized in that the salicylic acid ester of the above formula (5) formed by the terminal blocking reaction using a salicylic acid ester derivative expressed by the above formula (1)-2 as a terminal blocking agent or by the polymerization promoting reaction using a salicylic acid ester derivative expressed by the above formula (1)-2 wherein $R^2$ is an aryl group having a carbon number of from 6 to 30, an aryloxy group having a carbon number of from 6 to 30, an aralkyl group having a carbon number of from 6 to 30 or an aralkyloxy group having a carbon number of from 6 to 30 and may have, as a substituent, methoxycarbonyl group, ethoxycarbonyl group, 2-(methoxycarbonyl)phenyloxycarbonyl group, 2-(methoxycarbonyl)phenyloxycarbonyloxy group, 2-(ethoxycarbonyl)phenyloxycarbonyl group, or 2-(ethoxycarbonyl)phenyloxycarbonyloxy group as a polymerization promoting agent is recovered and the recovered salicylic ester is used in the production of an aromatic polycarbonate by a melt process.

53. A process for the production of a salicylic acid ester derivative described in claim 51 provided that the recovered salicylic acid ester is purified at least once and the purified salicylic acid is used in the production reaction.

54. A process for the production of a salicylic acid ester derivative described in claim 52 provided that the recovered salicylic acid ester is purified at least once and the purified salicylic acid is used in the production reaction.

55. A process for the production of an aromatic polycarbonate characterized by the use of a salicylic acid ester derivative described in claim 1 and claim 6 as a terminal blocking agent in the production of an aromatic polycarbonate by a melt process.

56. A process for the production of an aromatic polycarbonate characterized in that a salicylic acid ester derivative expressed by the above formula (1) wherein $R^2$ is an aryl group having a carbon number of from 6 to 30, an aryloxy group having a carbon number of from 6 to 30, an aralkyl group having a carbon number of from 6 to 30 or an aralkyloxy group having a carbon number of from 6 to 30 and may have, as a substituent, methoxycarbonyl group, ethoxycarbonyl group, 2-(methoxycarbonyl)phenyloxycarbonyl group, 2-(methoxycarbonyl)phenyloxycarbonyloxy group, 2-(ethoxycarbonyl)phenyloxycarbonyl group, or 2-(ethoxycarbonyl)phenyloxycarbonyloxy group is used as a polymerization promoting agent in a process for producing an aromatic polycarbonate by a melt process.

57. A process for the production of an aromatic polycarbonate characterized in that a salicylic acid ester derivative produced by a process described in claim 5 is used as a terminal blocking agent in the production of an aromatic polycarbonate by a melt process.

58. A process for the production of an aromatic polycarbonate characterized in that a salicylic acid ester derivative produced by a process described in claim 11 is used as a terminal blocking agent in the production of an aromatic polycarbonate by a melt process.

59. A process for the production of an aromatic polycarbonate characterized in that a salicylic acid ester derivative produced by a process described in claim 12 is used as a terminal blocking agent in the production of an aromatic polycarbonate by a melt process.

60. A process for the production of an aromatic polycarbonate characterized in that a salicylic acid ester derivative produced by a process described in claim 5 is used as a polymerization promoting agent in a process for producing an aromatic polycarbonate by a melt process.

61. A process for the production of an aromatic polycarbonate characterized in that a salicylic acid ester derivative produced by a process described in claim 11 is used as a polymerization promoting agent in a process for producing an aromatic polycarbonate by a melt process.

62. A process for the production of an aromatic polycarbonate characterized in that a salicylic acid ester derivative produced by a process described in claim 12 is used as a polymerization promoting agent in a process for producing an aromatic polycarbonate by a melt process.

63. An aromatic polycarbonate for optical material use obtained by a process to produce an aromatic polycarbonate by a melt process using a salicylic acid ester derivative produced by a process described in claim 5 as a terminal blocking agent and/or a polymerization promoting agent.

64. An aromatic polycarbonate for optical material use obtained by a process to produce an aromatic polycarbonate by a melt process using a salicylic acid ester derivative produced by a process described in claim 11 as a terminal blocking agent and/or a polymerization promoting agent.

65. An aromatic polycarbonate for optical material use obtained by a process to produce an aromatic polycarbonate by a melt process using a salicylic acid ester derivative produced by a process described in claim 12 as a terminal blocking agent and/or a polymerization promoting agent.

66. An aromatic polycarbonate described in claim 63 wherein the optical material use is the use as an optical disk substrate.

67. An aromatic polycarbonate described in claim 64 wherein the optical material use is the use as an optical disk substrate.

68. An aromatic polycarbonate described in claim 65 wherein the optical material use is the use as an optical disk substrate.

69. A salicylic acid ester derivative having a chlorine content of 10 ppm or below, the total nitrogen content is 100 ppm or below, the sum of the metallic elements contained in the derivative is 30 ppm or below, and expressed by the following formula (1)

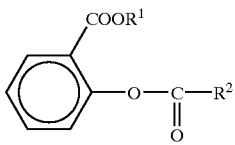

(1)

in the formula, $R^1$ is methyl group or ethyl group, $R^2$ is an alkyl group having a carbon number of from 1 to 30, an alkoxy group having a carbon number of from 1 to 30, an aryl group having a carbon number of from 6 to 30, an aryloxy group having a carbon number of from 6 to 30, an aralkyl group having a carbon number of from 6 to 30 or an aralkyloxy group having a carbon number of from 6 to 30; the group $R^2$ may have, as a substituent, methoxycarbonyl group, ethoxycarbonyl group, 2-(methoxycarbonyl) phenyloxycarbonyl group, 2-(methoxycarbonyl) phenyloxycarbonyloxy group, 2-(ethoxycarbonyl) phenyloxycarbonyl group, 2-(ethoxycarbonyl) phenyloxycarbonyloxy group or an aryloxycarbonyl group or aralkyloxycarbonyl group having a carbon number of from 6 to 10.

* * * * *